United States Patent [19]

Hayashi et al.

[11] 4,399,147
[45] Aug. 16, 1983

[54] PROSTAGLANDIN 12 ANALOGUES AND THEIR PHARMACEUTICAL COMPOSITIONS

[75] Inventors: Masaki Hayashi, Takatsuki; Yoshinobu Arai, Toyonaka; Yoshitaka Konishi; Katsuichi Shimoji, both of Takatsuki; Shuichi Ohuchida, Kyoto; Hirohisa Wakatsuka, Takatsuki; Hiroyuki Ito, Suita, all of Japan

[73] Assignee: Ono Pharmaceutical Co. Ltd., Japan

[21] Appl. No.: 872,635

[22] Filed: Jan. 26, 1978

[30] Foreign Application Priority Data

Jan. 31, 1977 [JP] Japan .................................. 52008751

[51] Int. Cl.$^3$ ................. A61K 31/557; C07D 307/935
[52] U.S. Cl. .................................... 424/285; 542/426; 542/429; 549/414; 549/465
[58] Field of Search .................... 260/346.22; 424/285; 542/426, 429; 549/465, 414

[56] References Cited

U.S. PATENT DOCUMENTS 3,978,229  8/1976  Matsumoto et al. ................. 424/275
4,045,468  8/1977  Kurono et al. ................. 260/346.22

OTHER PUBLICATIONS

Corey et al., J. Am. Chem. Soc. 99(6), Mar. 16, 1977, 2006-2008.
Pace-Asciak et al., Biochemistry, 10(20), (1971), pp. 3657-3663.

Primary Examiner—John M. Ford
Assistant Examiner—Bernard Dentz
Attorney, Agent, or Firm—Stevens, Davis, Miller & Mosher

[57] ABSTRACT

Prostaglandin I$_2$ analogues of the formula:

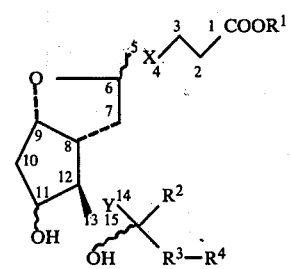

[wherein X represents trans-vinylene or an ethylene group unsubstituted or substituted by a bromine atom at the C-5 position, Y represents trans-vinylene or ethylene, R$^1$ represents hydrogen or an alkyl group containing from 1 to 12 carbon atoms, R$^2$ represents hydrogen or methyl or ethyl, R$^3$ represents a single bond or an alkylene group containing from 1 to 4 carbon atoms, R$^4$ represents hydrogen, an alkyl group containing from 1 to 8 carbon atoms, a cycloalkyl group containing from 4 to 7 carbon atoms unsubstituted or substituted by at least one alkyl group containing from 1 to 8 carbon atoms, or a phenyl or phenoxy group unsubstituted or carrying at least one substituent selected from halogen atoms, the trifluoromethyl group and alkyl groups containing from 1 to 3 carbon atoms, and the wavy line attached to the carbon atoms in positions 6, 11 and 15 depicted in the formula represents α- or β-configuration or mixtures thereof] are new compounds possessing pharmacological properties typical of prostaglandins, for example PGI$_2$, and are more stable than PGI$_2$.

13 Claims, No Drawings

PROSTAGLANDIN I2 ANALOGUES AND THEIR PHARMACEUTICAL COMPOSITIONS

This invention relates to new prostaglandin $I_2$ ($PGI_2$) analogues, to a process for their preparation and pharmaceutical compositions containing them.

$PGI_2$ is a physiologically active substance having the following formula:

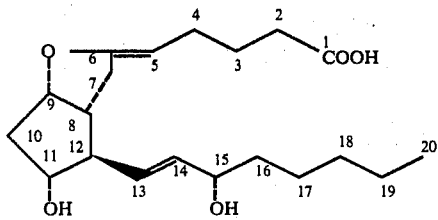

and its chemical name is (5Z,13E)-(9α,11α,15S)-6,9-epoxy-11,15-dihydroxyprosta-5,13-dienoic acid [Nature, 263, 663 (1976), Prostaglandins, 12, 685 (1976), ibid, 12, 915 (1976), ibid, 13, 3 (1977), ibid, 13, 375 (1977) and Chemical and Engineering News, Dec. 20, 17 (1976)].

It is well known that $PGI_2$ can be prepared by incubation of prostaglandin $G_2$ ($PGG_2$) or prostaglandin $H_2$ ($PGH_2$) with microsomal fractions prepared from thoracic aorta of swine, mesenteric artery of swine, rabbit aorta or the stomach fundus of rats. $PGI_2$ has a relaxing activity on the artery, which is peculier to the artery and which does not operate on other smooth muscle. Furthermore, $PGI_2$ strongly inhibits arachidonic acid-induced blood platelet aggregation of the human.

Taking into consideration that thromboxane $A_2$ (prepared by incubation of $PGG_2$ or $PGH_2$ with blood platelet microsome) has a contracting activity on the artery and an aggregating activity on blood platelets, the properties of $PGI_2$ heretofore mentioned show that $PGI_2$ fulfils a very important physiological part in a living body. $PGI_2$ may be useful in the treatment of arteriosclerosis, cardiac failure or thrombosis.

$PGI_2$ is a very unstable substance, for example $PGI_2$ becomes inactive in 20 minutes at 22° C. and in 10 minutes at 37° C. in a buffer solution at a pH 7.6. This instability is a serious drawback in adapting $PGI_2$ for medicinal purposes.

As a result of research and experimentation, we have prepared new analogues of $PGI_2$ which possess the useful pharmacological properties of $PGI_2$ but are much more stable.

The more stable $PGI_2$ analogues of the present invention are those compounds of the general formula:

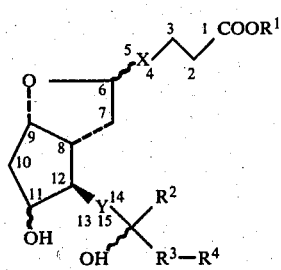

[wherein X represents the trans-vinylene group (i.e.

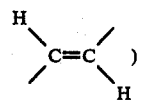

or an ethylene group unsubstituted or substituted by a bromine atom at the C-5 position (i.e.

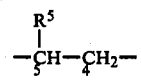

in which $R^5$ represents a hydrogen or bromine atom), Y represents the trans-vinylene group or the ethylene group, $R^1$ represents a hydrogen atom or a straight- or branched-chain alkyl group containing from 1 to 12 carbon atoms (preferably methyl), $R^2$ represents a hydrogen atom or a methyl or ethyl group, $R^3$ represents a single bond or a straight- or branched-chain alkylene group containing from 1 to 4 carbon atoms, $R^4$ represents a hydrogen atom, a straight- or branched-chain alkyl group containing from 1 to 8 carbon atoms, a cycloalkyl group containing from 4 to 7 carbon atoms unsubstituted or substituted by at least one straight- or branched-chain alkyl group containing from 1 to 8 carbon atoms, or a phenyl or phenoxy group unsubstituted or carrying at least one substituent selected from halogen atoms, the trifluoromethyl group and alkyl groups containing from 1 to 3 carbon atoms, and the wavy line attached to the carbon atoms in positions 6, 11 and 15 depicted in formula II represents α- or β-configuration (i.e. S- or R-configuration) or mixtures thereof], and cyclodextrin clathrates of such acids and esters and, when $R^1$ represents a hydrogen atom, non-toxic (e.g. sodium) salts thereof. Preferred compounds are those of general formula II wherein X represents an ethylene group unsubstituted or substituted by a bromine atom at the C-5 position.

The present invention is concerned with all compounds of general formula II in the 'natural' form or its enantiomeric form, or mixtures thereof, more particularly the racemic form, consisting of equimolecular mixtures of 'natural' form and its enantiomeric form.

As will be apparent to those skilled in the art, the compounds depicted in general formula II have at least six centres of chirality, these six centres of chirality being at the C-6, C-8, C-9, C-11, C-12 and C-15 carbon atoms. Still further centres of chirality may occur when $R^1$ or $R^4$ is a branched-chain alkyl group, $R^3$ is a branched-chain alkylene group or X is a bromo-substituted ethylene group. The presence of chirality leads as is well known to the existence of isomerism. However, the compounds of general formula II all have such a configuration that the substituent groups attached to the ring carbon atoms in the positions identified as 8 and 12 are trans with respect to each other and that the substituent groups attached to the ring carbon atoms in the positions identified as 8 and 9 are cis with respect to each other. The groups attached to the carbon atom in the 6-position are in S- or R-configuration.

Accordingly, all isomers of general formula II and mixtures thereof which have those substituent groups attached to the ring carbon atoms in positions 8 and 12 in the trans-configuration, those attached in positions 8 and 9 in the cis-configuration, and to the carbon atom in the 6-position in S- or R-configuration are to be considered within the scope of general formula II.

Preferably —R³—R⁴ represents pentyl, 1-methylpentyl, 2-methylpentyl, 3-methylpentyl, 4-methylpentyl, 1,1-dimethylpentyl, 1,2-dimethylpentyl, 1,4-dimethylpentyl, 1-ethylpentyl, 2-ethylpentyl, 1-propylpentyl, 2-propylpentyl, hexyl, 1-methylhexyl, 2-methylhexyl, 1,1-dimethylhexyl, 1-ethylhexyl, 2-ethylhexyl, heptyl, 2-ethylheptyl, nonyl, undecyl, cyclobutyl, (1-propyl)-cyclobutyl, (1-butyl)cyclobutyl, (1-pentyl)-cyclobutyl, (2-propyl)cyclobutyl, (3-ethyl)cyclobutyl, (3-propyl)-cyclobutyl, cyclopentyl, 1-cyclopentylethyl, 2-cyclopentylethyl, 2-cyclopentylpropyl, (3-ethyl)cyclopentyl, (3-propyl)cyclopentyl, (3-butyl)cyclopentyl, (1-methyl-3-propyl)cyclopentyl, (2-methyl-3-propyl)-cyclopentyl, cyclohexyl, (3-ethyl)cyclohexyl, (4-methyl)cyclohexyl, (4-ethyl)-cyclohexyl, (4-propyl)cyclohexyl, (2,6-dimethyl)cyclohexyl, cyclohexylmethyl, (1-methylcyclohexyl)methyl, 1-cyclohexylethyl, 2-cyclohexylethyl, (1-methyl-1-cyclohexyl)ethyl, 1-cycloheptylethyl, phenyl, benzyl, 1-phenylethyl, 2-phenylethyl, 1-phenylpentyl, phenoxymethyl, (3-chlorophenoxy)methyl, (4-chlorophenoxy)methyl or (3-trifluoromethylphenoxy)methyl.

According to a feature of the present invention, the prostaglandin analogues of general formula II, wherein the various symbols are as hereinbefore defined, are prepared by the process which comprises hydrolyzing to hydroxy groups the groups OR⁶ of a compound of the general formula:

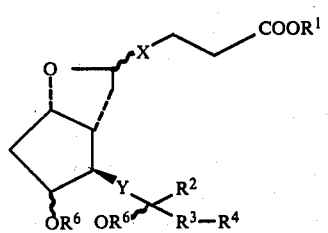

(wherein R⁶ represents a tetrahydropyran-2-yl group unsubstituted or substituted by at least one alkyl group, or a tetrahydrofuran-2-yl or 1-ethoxyethyl group, and the other symbols are as hereinbefore defined) under mild acidic conditions.

The groups OR⁶ of the compounds of general formula III may be converted to hydroxy groups by mild acidic hydrolysis (1) with an aqueous solution of an organic acid such as acetic acid, propionic acid, oxalic acid, or p-toluenesulphonic acid, or an aqueous solution of an inorganic acid, such as hydrochloric acid or sulphuric acid, advantageously in the presence of an inert organic solvent miscible with water, e.g. a lower alkanol such as methanol or ethanol (preferably methanol), or an ether such as 1,2-dimethoxyethane, dioxan, or tetrahydrofuran (preferably tetrahydrofuran), at a temperature ranging from ambient to 75° C. (preferably at a temperature below 45° C.), or (2) with an anhydrous solution of an organic acid such as p-toluenesulphonic acid or trifluoroacetic acid in a lower alkanol such as methanol or ethanol at a temperature ranging from 10° to 45° C. Advantageously the mild hydrolysis may be carried out with a mixture of hydrochloric acid, water and tetrahydrofuran, a mixture of hydrochloric acid, water and methanol, a mixture of acetic acid, water and tetrahydrofuran, or a mixture of p-toluenesulphonic acid and methanol. The product of general formula II thus obtained is a mixture of isomers in which the groups attached to the carbon atom at position 6 are in S- and R-configurations. If desired, the mixture may be separated by column chromatography on silica gel, or thin layer chromatography on silica gel, to give each of the isomers.

Compounds of general formula III, wherein X represents an ethylene group substituted by a bromine atom at the C-5 position and the other symbols are as hereinbefore defined, i.e. compounds of the general formula:

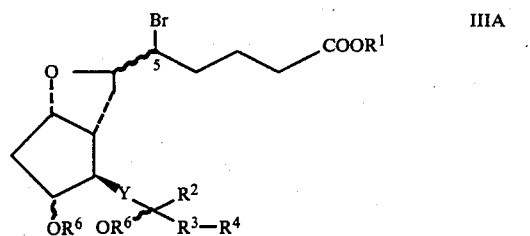

(wherein the various symbols are as hereinbefore defined), may be prepared by bromination of a compound of the general formula:

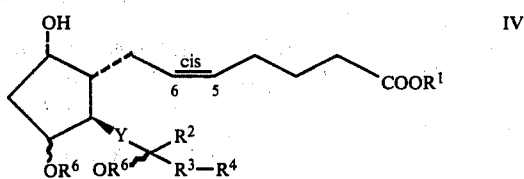

(wherein the various symbols are as hereinbefore defined) and subsequent cyclization of the resulting brominated compound. The conversion of the compound of general formula IV to a compound of general formula IIIA may be suitably carried out with N-bromosuccinimide or N-bromoacetamide in an aprotic organic solvent, e.g. methylene chloride, chloroform, carbon tetrachloride, diethyl ether, N,N-dimethylformamide or tetrahydrofuran, or a mixture of two or more of them, at a temperature of from −30° to 70° C. The product of general formula IIIA thus obtained is a mixture of isomers in which the absolute configurations of C₅ and C₆ are (5R,6R) and (5S,6S). If desired, the mixture may be separated by column chromatography on silica gel or thin layer chromatography on silica gel to give each of the isomers.

Compounds of general formula III wherein X represents an unsubstituted ethylene group and the other symbols are as hereinbefore defined, i.e. compounds of the general formula:

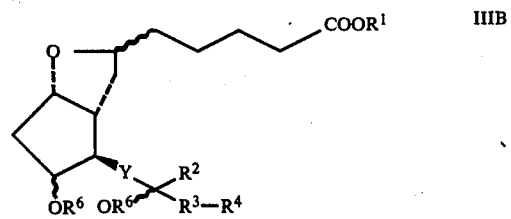

(wherein the various symbols are as hereinbefore defined), may be prepared from a compound of general formula IIIA (1) by photochemical reaction with light from a high pressure mercury lamp in the presence of tri-n-butyltin hydride and 2,2'-azobisisobutyronitrile in benzene at room temperature, or (2) by reaction with sodium cyanoborohydride in the presence of hexamethylphosphamide at a temperature of from 70° to 100° C., preferably at 70° C. [cf. Chemical Communications, 1097 (1971)].

Compounds of general formula III wherein X represents the trans-vinylene group and the other symbols are as hereinbefore defined, i.e. compounds of the general formula:

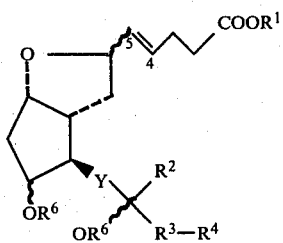 IIIC (wherein the various symbols are as hereinbefore defined, and the depicted $C_4$-$C_5$ double bond is trans), may be prepared from a compound of general formula IIIA via compounds of the general formula:

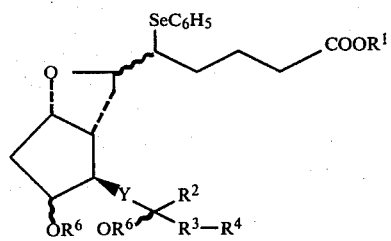 V wherein the various symbols are as hereinbefore defined.

The conversion of compounds of general formula IIIA to those of general formula V may be carried out by reaction with diphenyldiselenide (i.e. $C_6H_5SeSeC_6H_5$) and sodium borohydride in the presence of a lower alkanol (preferably methanol or ethanol) at a temperature between the ambient and the reflux temperature of the reaction mixture.

The conversion of compounds of general formula V to those of general formula IIIC may be carried out by reaction (1) with hydrogen peroxide in a mixture of ethyl acetate and tetrahydrofuran or ethyl acetate and methanol, preferably in the presence of sodium bicarbonate, at a temperature below 30° C., or (2) with sodium periodate in a mixture of water and a lower alkanol, e.g. methanol or ethanol, preferably in the presence of sodium bicarbonate at a temperature below 30° C.

The compounds of general formula II wherein X represents the ethylene group and the other symbols are as hereinbefore defined, i.e. compounds of the general formula:

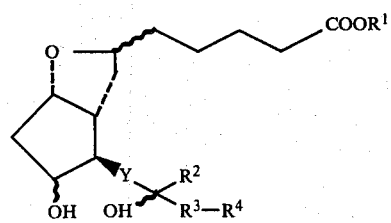 IIB (wherein the various symbols are as hereinbefore defined) may also be prepared from compounds of general formula II wherein X represents a bromoethylene group i.e.

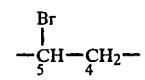

and the other symbols are as hereinbefore defined, i.e. compounds of the general formula:

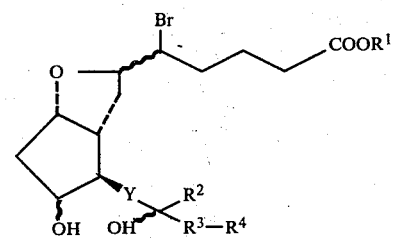 IIA (wherein the various symbols are as hereinbefore defined) by means heretofore mentioned for the conversion of compounds of general formula IIIA to those of general formula IIIB.

Compounds of general formula IIA may also be prepared from compounds of the general formula:

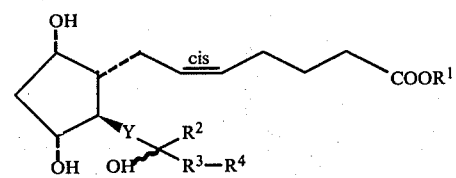 VI (wherein the various symbols are as hereinbefore defined) by means heretofore mentioned for the conversion of compounds of general formula IV to those of general formula IIIA.

The compounds of general formula V may also be prepared from the compounds of general formula IV by treatment with benzeneselenenyl bromide ($C_6H_5SeBr$) in the presence of calcium carbonate in an inert organic solvent, e.g. tetrahydrofuran, at a moderately low temperature, for example at 0° C.

The compounds of general formula II wherein Y represents the ethylene group, and the other symbols are as hereinbefore defined, may also be prepared by reduction of compounds of general formula II wherein Y represents the trans-vinylene group and the other symbols are as hereinbefore defined. Suitably, the reduction may be effected by hydrogenation in the presence of a hydrogenation catalyst, for example palladium on charcoal, palladium black or platinum dioxide, in the presence of an inert organic solvent, for example a lower alkanol, e.g. methanol or ethanol, at laboratory temperature at normal or elevated pressure, e.g. at a hydrogen pressure from atmospheric to 15 kilogrammes per square centimeter.

According to another feature of the present invention, the compounds of general formula II wherein $R^1$ represents a hydrogen atom and the other symbols are as hereinbefore defined, i.e. compounds of the general formula:

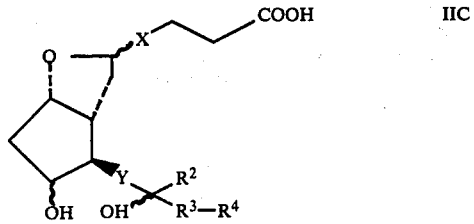
IIC (wherein the various symbols are as hereinbefore defined) may be prepared by (1) the hydrolysis under alkaline conditions of a compound of general formula II wherein $R^1$ represents a straight- or branched-chain alkyl group containing from 1 to 12 carbon atoms and the other symbols are as hereinbefore defined, i.e. compounds of the general formula:

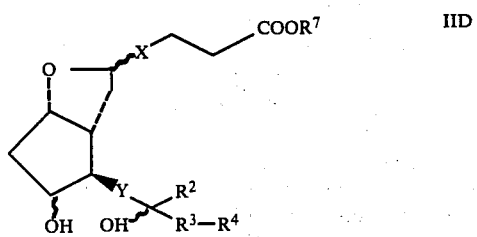
IID (wherein $R^7$ represents a straight- or branched-chain alkyl group containing from 1 to 12 carbon atoms and the other symbols are as hereinbefore defined), or (2) the hydrolysis under alkaline conditions of a compound of general formula III, wherein $R^1$ represents a straight- or branched-chain alkyl group containing from 1 to 12 carbon atoms and the other symbols are as hereinbefore defined, and then treatment of the resulting compound of general formula III, wherein $R^1$ represents a hydrogen atom and the other symbols are as hereinbefore defined, by means heretofore mentioned for the conversion of a compound of general formula III to a compound of general formula II.

The hydrolysis under alkaline conditions may be effected with an aqueous solution of an alkaline metal, e.g. sodium or potassium, hydroxide or carbonate in the presence of a water miscible solvent, e.g. tetrahydrofuran or a lower alkanol.

Starting materials of general formulae IV and VI may be prepared by the methods described in the following patent specifications and applications, or obvious modifications thereof:

(1) when $R^2$ is a hydrogen atom or a methyl or ethyl group and the grouping —$R^3$—$R^4$ is a straight- or branched-chain alkyl group, as described in Japanese Pat. Kokai Nos. 49-124048, 49-134656, 50-13362, 50-25549, 50-101340 and 51-68547, British Pat. Nos. 1,398,291, 1,450,691, 1,464,916 and 1,483,240, and U.S. Pat. Nos. 3,962,312, 3,966,792 and 4,024,174;

(2) when $R^2$ is a hydrogen atom or a methyl or ethyl group, $R^3$ is a single bond or a straight- or branched-chain alkylene group and $R^4$ is an unsubstituted or substituted cycloalkyl group, as described in Japanese Pat. Kokai Nos. 50-13364, 50-25549, 50-148339 and 51-68547, British Pat. Nos. 1,450,691, 1,464,916, 1,488,141, 1,483,240 and 1,484,210, British patent applications Nos. 30072/75 and 18651/76, U.S. Pat. Nos. 3,962,312, 3,966,792, 4,034,003, 4,024,174 and 4,045,468, U.S. application Ser. No. 703,158 and Belgian Pat. No. 844256;

(3) when $R^2$ is a hydrogen atom or a methyl or ethyl group, $R^3$ is a single bond or a straight- or branched-chain alkylene group and $R^4$ is an unsubstituted or substituted phenyl group, as described in Japanese Pat. Kokai Nos. 50-13364, 50-25549 and 51-68547, British Pat. Nos. 1,450,691 and 1,483,240 and U.S. Pat. Nos. 3,962,312 and 4,024,174;

(4) when $R^2$ is a hydrogen atom or a methyl or ethyl group, $R^3$ is a single bond or a straight- or branched-chain alkylene group and $R^4$ is an unsubstituted or substituted phenoxy group, as described in Japanese Pat. Kokai No. 51-59841 or 52-25745, British patent applications Nos. 34688/75 and 43464/75, U.S. application Ser. No. 713,941 and Belgian Pat. No. 845358;

(5) when $R^2$ is a hydrogen atom, $R^3$ is a single bond and $R^4$ is a hydrogen atom, from compounds of general formula VII depicted hereafter, which may be prepared as described in British Pat. No. 1,482,928, by the series of reactions depicted schematically below in Scheme A, wherein $R^8$ represents an alkanoyl group containing from 2 to 5 carbon atoms and the other symbols are as hereinbefore defined.

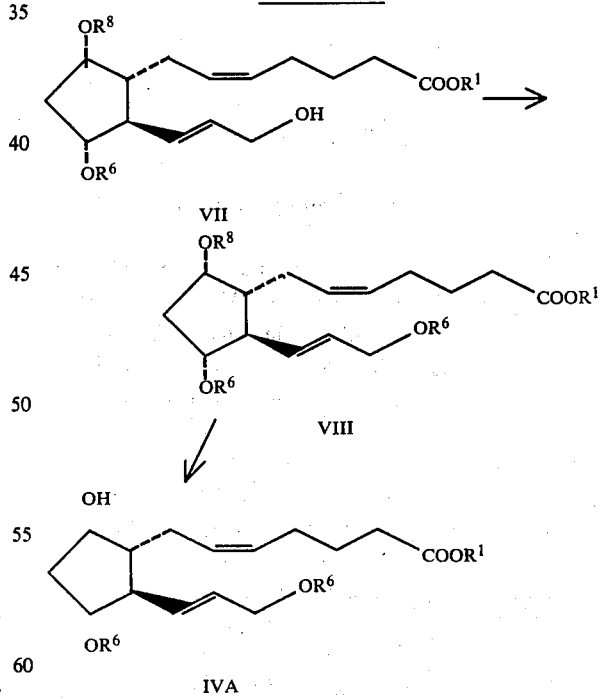

SCHEME A

Compounds of the general formula VII may be converted into compounds of general formula VIII by reaction with a dihydropyran, dihydrofuran or ethyl vinyl ether in an inert solvent, e.g. methylene chloride, in the presence of a condensing agent, e.g. p-toluenesulphonic acid.

Compounds of the general formula VIII may be converted into compounds of the general formula IVA by hydrolysis under alkaline conditions, which may be effected with anhydrous potassium carbonate in an anhydrous lower alkanol, preferably absolute methanol.

The qualification "lower" as applied herein to alkanols means that the alkanol contains at most four carbon atoms.

The compounds of general formulae III (viz. those of general formulae IIIA, IIIB and IIIC) and V are new compounds and as such constitute further features of the invention.

Esters of the prostaglandin analogues of general formula II, i.e. compounds of general formula II wherein $R^1$ represents a straight- or branched-chain alkyl group containing from 1 to 12 carbon atoms and the other symbols are as hereinbefore defined, may be prepared by esterification of the corresponding acid of general formula II wherein $R^1$ represents a hydrogen atom by methods known per se (i.e. methods hereinbefore used or described in the chemical literature), for example by reaction with (i) the appropriate diazoalkane in an inert organic solvent, e.g. diethyl ether, at a temperature of from $-10°$ to $25°$ C. and preferably $0°$ C., (ii) the appropriate alcohol in the presence of dicyclohexylcarbodiimide as condensing agent, or (iii) the appropriate alcohol following formation of a mixed anhydride by adding a tertiary amine and pivaloyl halide or an alkylsulphonyl or arylsulphonyl halide (cf. our British Pat. Nos. 1,362,956 and 1,364,125).

Compounds of general formula II wherein $R^1$ represents a hydrogen atom may, if desired, be converted by methods known per se into non-toxic salts.

By the term "non-toxic salts", as used in this specification, is meant salts the cations of which are relatively innocuous to the animal organism when used in therapeutic doses so that the beneficial pharmacological properties of the compounds of general formula II are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acids are well known and include, for example, amines derived in theory by the replacement of one or more of the hydrogen atoms or ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

The non-toxic salts may be prepared from acids of general formula II wherein $R^1$ represents a hydrogen atom by, for example, reaction of stoichiometric quantities of an acid of general formula II and the appropriate base, e.g. an alkali metal hydroxide or carbonate, ammonium hydroxide, ammonia or an amine, in a suitable solvent. The salts may be isolated by lyophilisation of the solution, or, if sufficiently insoluble in the reaction medium, by filtration, if necessary after removal of part of the solvent.

Cyclodextrin clathrates of the prostaglandin analogues of general formula II may be prepared by dissolving the cyclodextrin in water or an organic solvent which is miscible with water and adding to the solution the prostaglandin analogue in a water-miscible organic solvent. The mixture is then heated and the desired cyclodextrin clathrate product isolated by concentrating the mixture under reduced pressure or by cooling and separating the product by filtration or decantation. The ratio of organic solvent to water may be varied according to the solubilities of the starting materials and products. Preferably the temperature is not allowed to exceed $70°$ C. during the preparation of the cyclodextrin clathrates. $\alpha$-, $\beta$- or $\gamma$-Cyclodextrins or mixtures thereof may be used in the preparation of the cyclodextrin clathrates. Conversion into their cyclodextrin clathrates serves to increase the stability of the prostaglandin analogues.

The prostaglandin analogues of general formula II and their cyclodextrin clathrates and, when $R^1$ represents a hydrogen atom, non-toxic salts possess the valuable pharmacological properties typical of the prostaglandins in a selective fashion, in particular hypotensive activity, inhibitory activity on blood platelet aggregation, relaxing activity of artery, inhibitory activity on gastric acid secretion and gastric ulceration, stimulatory activity on uterine contraction and abortifacient, luteolytic and antinidatory activity, and are useful in the treatment of hypertension, in the treatment of disorders of the peripheral circulation, in the prevention and treatment of cerebral thrombosis, myocardial infarction and arteriosclerosis, in the treatment of gastric ulceration, in the termination of pregnancy and induction of labour in pregnant female mammals and in the treatment of impaired fertility, in the control of oestrus, contraception and menstrual regulation in female mammals. For example, in standard laboratory tests, (i) by intravenous administration to the allobarbital-anaesthetized dog, (13E)-(5RS,6RS,9α,11α,15S)-5-bromo-6,9-epoxy-11,15-dihydroxyprost-13-enoic acid methyl ester produces a fall in blood pressure of 18 mm Hg and 40 mm Hg lasting 11 and 35 minutes at the doses of 10 and 50 μg/kg animal body weight, respectively, (13E)-(5RS,6RS,9α,11α,15S)-5-bromo-6,9-epoxy-11,15-dihydroxyprost-13-enoic acid produces a fall in blood pressure of 38 mm Hg and 60 mm Hg lasting 7 and 13 minutes at the doses of 10 and 20 μg/kg animal body weight, respectively, (13E)-(5RS,6RS,9α,11α,15S,16S)-5-bromo-6,9-epoxy-11,15-dihydroxy-16-methylprost-13-enoic acid produces a fall in the blood pressure of 24 mm Hg and 50 mm Hg lasting 9 and 23 minutes at the doses of 5 and 10 μg/kg animal body weight, respectively, (13E)-(6RS,9α,11α,15S)-6,9-epoxy-11,15-dihydroxyprost-13-enoic acid methyl ester produces a fall in blood pressure of 16 mm Hg and 60 mm Hg lasting 16 and 53 minutes at the doses of 10 and 50 μg/kg animal body weight, respectively, (13E)-(6RS,9α,11α,15S)-6,9-epoxy-11,15-dihydroxyprost-13-enoic acid produces a fall in blood pressure of 22 mm Hg and 38 mm Hg lasting 8 and 7 minutes at the doses of 5 and 10 μg/kg animal body weight, respectively, (13E)-(6RS,9α,11α,15S,16S)-6,9-epoxy-11,15-dihydroxy-16-methylprost-13-enoic acid produces a fall in blood pressure of 26 mm Hg and 30 mm Hg lasting 6 and 8 minutes at the doses of 2 and 4 μg/kg animal body weight, respectively, (4E,13E)-(6RS,9α,11α,15S)-6,9-epoxy-11,15-dihydroxyprosta-4,13-dienoic acid produces a fall in blood pressure of 30 mm Hg lasting 6 minutes at the dose of 50 μg/kg body weight, (13E)-(6RS,9α,11α,15S)-6,9-epoxy-11,15-dihydroxy-15-(3-propylcyclopentyl)-16,17,18,19,20-pentanorprost-13-enoic acid methyl ester produces a fall in blood pressure of 14 mm Hg and 44 mm Hg lasting 6 and 6 minutes at the doses of 2 and 5 μg/kg animal body weight, respectively, (13E)-(6RS,9α,11α,15RS)-6,9-epoxy-11,15-dihydroxy- 15-methylprost-13-enoic acid methyl ester produces a fall in blood pressure of 13 mm Hg lasting 18 minutes at the dose of 30 μg/kg animal body weight, (13E)-(6RS,9α,11α,15S,16RS)-6,9-epoxy-11,15-dihydroxy-16-cyclopentyl-18,19,20-trinorprost-13-enoic acid methyl ester produces a fall in blood pressure of 24 mm Hg lasting 8 minutes at the dose of 50 μg/kg animal body weight, (13E)-(6RS,9α,11α,15S,16R)-6,9-epoxy-11,15-dihydroxy-16-methylprost-13-enoic acid produces a fall in blood pressure of 14 mm Hg and 38 mm Hg lasting 7 and 28 minutes at the doses of 1 and 3 μg/kg animal body weight, respectively, and (13E)-(6RS,9α,1-1α,15S)-6,9-epoxy-11,15-dihydroxy-15-cyclohexyl-16,17,18,19,20-pentanorprost-13-enoic acid methyl ester produces a fall in blood pressure of 14 mm Hg and 20 mm Hg lasting 38 and 15 minutes at the doses of 10 and 30 μg/kg animal body weight, (ii) (13E)-(6RS,9α,1-1α,15S)-6,9-epoxy-11,15-dihydroxyprost-13-enoic acid, (13E)-(6RS,9α,11α,15S)-6,9-epoxy-11,15-dihydroxyprost-13-enoic acid methyl ester, (13E)-(6RS,9α,1-1α,15S,16S)-6,9-epoxy-11,15-dihydroxy-16-methylprost-13-enoic acid, (13E)-(6RS,9α,11α,15S)-6 9-epoxy-11,15-dihydroxy-15-(3-propylcyclopentyl)-16,17,18,19,20-pentanorprost-13-enoic acid methyl ester, (13E)-(6RS,9α,11α,15S,16RS)-6,9-epoxy-11,15-dihydroxy-16-cyclopentyl-18,19,20-trinorprost-13-enoic acid methyl ester, (13E)-(6RS,9α,11α,15S,16R)-6,9-epoxy-11,15-dihydroxy-16-methylprost-13-enoic acid, (13E)-(6RS,9α,11α,15S)-6,9-epoxy-11,15-dihydroxy-15-cyclohexyl-16,17,18,19,20-pentanorprost-13-enoic acid methyl ester and (13E)-(6RS,9α,1-1α,15S,17S)-6,9-epoxy-11,15-dihydroxy-17,20-dimethylprost-13-enoic acid methyl ester produce a 50% inhibition of adenosine diphosphate-induced blood platelet aggregation in platelet-rich plasma of rats at the concentrations of $4.8\times10^{-1}$, $5.7\times10^{-1}$, $1.65\times10^{-1}$, $6.2\times10^{-2}$, $6.0\times10^{-1}$, $2.2\times10^{-1}$, $5.1\times10^{-2}$ and $2.0\times10^{-2}$ μg/ml, respectively, in comparison with controls, (iii) (13E)-(5RS,6RS,9α,11α,15S,16S)-5-bromo-6,9-epoxy-11,15-dihydroxy-16-methylprost-13-enoic acid, (13E)-(6RS,9α,11α,15S)-6,9-epoxy-11,15-dihydroxyprost-13-enoic acid and (13E)-(6RS,9α,1-1α,15R)-6,9-epoxy-11,15-dihydroxy-16,16-dimethylprost-13-enoic acid relax mesenteric artery of rabbit contracted by noradrenalin at the concentrations of $5\times10^{-7}$ to $1\times10^{-5}$, $2\times10^{-6}$ to $5\times10^{-5}$ and $1\times10^{-5}$ to $5\times10^{-5}$ g/ml, respectively, and (iv) (13E)-(5RS,6RS,9α,11α,15S)-5-bromo-6,9-epoxy-11,15-dihydroxyprost-13-enoic acid methyl ester, (13E)-(5RS,6RS,9α,11α,15R)-5-bromo-6,9-epoxy-11,15-dihydroxy-16,16-dimethylprost-13-enoic acid, (13E)-(5RS,6RS,9α,11α,15S,16S)-5-bromo-6,9-epoxy-11,15-dihydroxy-16-methylprost-13-enoic acid, (4E,13E)-(6RS,9α,11α,15S)-6,9-epoxy-11,15-dihydroxyprost-4,13-dienoic acid methyl ester, (4E,13E)-(6RS,9α,1-1α,15S)-6,9-epoxy-11,15-dihydroxyprosta-4,13-dienoic acid, (13E)-(6RS,9α,11α,15S)-6,9-epoxy-11,15-dihydroxyprost-13-enoic acid methyl ester, (13E)-(6RS,9α,11α,15S)-6,9-epoxy-11,15-dihydroxyprost-13-enoic acid, (13E)-(6RS,9α,11α,15R)-6,9-epoxy-11,15-dihydroxy-16,16-dimethylprost-13-enoic acid, (13E)-(6RS,9α,11α,15S,16S)-6,9-epoxy-11,15-dihydroxy-16-methylprost-13-enoic acid, (13E)-(6RS,9α,11α,15S)-6,9-epoxy-11,15-dihydroxy-15-(3-propylcyclopentyl)-16,17,18,19,20-pentanorprost-13-enoic acid methyl ester, (13E)-(6RS,9α,11α,15R)-6,9-epoxy-11,15-dihydroxy-16-(3-chlorophenoxy)-17,18,19,20-tetranorprost-13-enoic acid methyl ester and (13E)-(6RS,9α,1-1α,15R)-6,9-epoxy-11,15-dihydroxy-16,16-dimethylprost-13-enoic acid methyl ester stimulate uterine contraction in the pregnant female rat when administered intravenously on the 20th day of gestation at the doses of 50 to 100, 5 to 10, 5, 20 to 50, 10 to 20, 20, 20, 10, 5, 40 to 100, 10 and 2 to 5 μg/kg animal body weight respectively.

Moreover, the compounds of general formula II wherein X represents a bromoethylene group and the other symbols are as hereinbefore defined, i.e. the compounds of the general formula IIA, are also useful as intermediates for the preparation of prostaglandin $I_2$ analogues.

The following Reference Examples and Examples illustrate, but not limit, the preparation of new prostaglandin analogues of the present invention. In them 'TLC', 'IR', 'NMR' and 'MASS' represent respectively 'Thin layer chromatography', 'Infrared absorption spectrum', 'Nuclear magnetic resonance spectrum' and 'Mass spectrum'. Where solvent ratios are specified in chromatographic separations, the ratios are by volume.

REFERENCE EXAMPLE 1

(5Z,13E)-(9α,11α)-9-Acetoxy-11,15-bis(tetrahydropyran-2-yloxy)-16,17,18,19,20-pentanorprosta-5,13-dienoic acid methyl ester To a solution of 2.2 g of (5Z,13E)-(9α,11α)-9-acetoxy-11-(tetrahydropyran-2-yloxy)-15-hydroxy-16,17,18,19,20-pentanorprosta-5,13-dienoic acid methyl ester in 20 ml of methylene chloride were added 50 mg of p-toluenesulphonic acid and 0.564 ml of 2,3-dihydropyran and the mixture was stirred at room temperature for 30 minutes. The reaction mixture was then neutralised with an aqueous solution of sodium bicarbonate, diluted with ethyl acetate, washed with water and an aqueous solution of sodium chloride, dried over magnesium sulphate and concentrated under reduced pressure. The residue was purified by column chromatography on silica gel using a mixture of cyclohexane and ethyl acetate (2:1) as eluent to give 2.06 g of the title compound having the following physical characteristic:

TLC (developing solvent, benzene:ethyl acetate=2:1): Rf=0.64.

REFERENCE EXAMPLE 2

(5Z,13E)-(9α,11α)-9-Hydroxy-11,15-bis(tetrahydropyran-2-yloxy)-16,17,18,19,20-pentanorprosta-5,13-dienoic acid methyl ester A solution of 2 g of (5Z,13E)-(9α,11α)-9-acetoxy-11,15-bis(tetrahydropyran-2-yloxy)-16,17,18,19,20-pentanorprosta-5,13-dienoic acid methyl ester (prepared as described in Reference Example 1) in 20 ml of dry methanol was stirred with 617 mg of anhydrous potassium carbonate at room temperature for 3 hours, then cooled to 0° C., and acidified with acetic acid. The reaction mixture was diluted with ethyl acetate, washed with an aqueous solution of sodium bicarbonate and an aqueous solution of sodium chloride, dried over magnesium sulphate and concentrated under reduced pressure. The residue was purified by column chromatography on silica gel using a mixture of cyclohexane and ethyl acetate (2:1) as eluent to give 1.7 g. of the title compound having the following physical characteristic:

TLC (developing solvent, benzene:ethyl acetate=2:1): Rf=0.51.

EXAMPLE 1

(13E)-(5RS,6RS,9α,11α,15S)-5-Bromo-6,9-epoxy-11,15-bis(tetrahydropyran-2-yloxy)prost-13-enoic acid methyl ester Under an atmosphere of nitrogen, a solution of 3.4 g of (5Z,13E)-(9α,11α,15S)-9-hydroxy-11,15-bis(tetrahydropyran-2-yloxy)prosta-5,13-dienoic acid methyl ester in a mixture of 30 ml of methylene chloride and 6 ml of N,N-dimethylformamide was added dropwise to a suspension of 1.35 g of N-bromosuccinimide in 50 ml of methylene chloride at −20° to −10° C. and the mixture was stirred for 30 minutes at the same temperature. The reaction mixture was then poured into ice-water and extracted with diethyl ether. The extract was washed with water and an aqueous solution of sodium chloride, dried over magnesium sulphate and concentrated under reduced pressure. The residue was purified by column chromatography on silica gel using a mixture of cyclohexane and ethyl acetate (4:1) as eluent to give 3.43 g of the title compound having the following physical characteristics:

TLC (developing solvent, benzene:ethyl acetate=2:1): Rf=0.65 and 0.69;

IR (liquid film): $\nu$=1745, 1440, 1030, 980 cm$^{-1}$;

NMR (CDCl$_3$ solution): δ=5.72–5.30 (2H, m), 4.80–4.46 (3H, m), 4.32–2.32 (11H, m), 1.00–0.75 (3H, m).

The following compounds were obtained following the same procedure as described above.

(a) (13E)-(5RS,6RS,9α,11α,15S)-5-Bromo-6,9-epoxy-11,15-bis(tetrahydropyran-2-yloxy)prost-13-enoic acid, having the following physical characteristics, was prepared from (5Z,13E)-(9α,11α,15S)-9-hydroxy-11,15-bis(tetrahydropyran-2-yloxy)-prosta-5,13-dienoic acid.

TLC (developing solvent, ethyl acetate:formic acid=400:5): Rf=0.55;

IR (liquid film): $\nu$=1710, 1440, 1020, 980 cm$^{-1}$;

NMR (CDCl$_3$ solution): δ=8.70 (1H, broad s), 5.70–5.25 (2H, m), 4.80–4.45 (3H, m), 4.23–3.25 (8H, m), 1.02–0.70 (3H, m).

(b) (13E)-(5RS,6RS,9α,11α,15S,16S)-5-Bromo-6,9-epoxy-11,15-bis(tetrahydropyran-2-yloxy)-16-methylprost-13-enoic acid, having the following physical characteristics, was prepared from (5Z,13E)-(9α,11α,15S,16S)-9-hydroxy-11,15-bis(tetrahydropyran-2-yloxy)-16-methylprosta-5,13-dienoic acid.

TLC (developing solvent, benzene:ethyl acetate:methanol=19:38:1): Rf=0.45 and 0.54;

IR (liquid film): $\nu$=1710, 1440, 1020, 980 cm$^{-1}$;

NMR (CDCl$_3$ solution): δ=8.70 (1H, broad s), 5.70–5.25 (2H, m), 4.80–4.45 (3H, m), 4.23–3.25 (8H, m), 1.02–0.75 (6H, m).

(c) (13E)-(5RS,6RS,9α,11α,15R)-5-Bromo-6,9-epoxy-11,15-bis(tetrahydropyran-2-yloxy)-16,16-dimethylprost-13-enoic acid, having the following physical characteristics, was prepared from (5Z,13E)-(9α,11α,15R)-9-hydroxy-11,15-bis(tetrahydropyran-2-yloxy)-16,16-dimethylprosta-5,13-dienoic acid.

TLC (developing solvent, benzene:ethyl acetate:methanol=19:38:1): Rf=0.59 and 0.68;

IR (liquid film): $\nu$=1710, 1440, 1020, 980 cm$^{-1}$;

NMR (CDCl$_3$ solution): δ=8.90 (1H, broad s), 5.70–5.25 (2H, m), 4.80–4.45 (3H, m), 4.23–3.25 (8H, m), 1.02–0.70 (9H, m).

(d) (13E)-(5RS,6RS,9α,11α,15R)-5-Bromo-6,9-epoxy-11,15-bis-(tetrahydropyran-2-yloxy)-16-phenoxy-17,18,19,20-tetranorprost-13-enoic acid, having the following physical characteristics, was prepared from (5Z,13E)-(9α,11α,15R)-9-hydroxy-11,15-bis(tetrahydropyran-2-yloxy)-16-phenoxy-17,18,19,20-tetranorprosta-5,13-dienoic acid.

IR (liquid film): $\nu$=1710, 1600, 1590, 1500, 1440, 1250, 980, 760 cm$^{-1}$;

NMR (CDCl$_3$ solution): δ=8.70 (1H, broad s), 7.40–6.80 (5H, m), 5.76–5.30 (2H, m), 4.80–4.45 (4H, m), 4.22–3.25 (9H, m).

(e) (13E)-(5RS,6RS,9α,11α,15R)-5-Bromo-6,9-epoxy-11,15-bis(tetrahydropyran-2-yloxy)-16-(3-chlorophenoxy)-17,18,19,20-tetranorprost-13-enoic acid methyl ester, having the following physical characteristics, was prepared from (5Z,13E)-(9α,11α,15R)-9-hydroxy-11,15-bis(tetrahydropyran-2-yloxy)-16-(3-chlorophenoxy)-17,18,19,20-tetranorprosta-5,13-dienoic acid methyl ester.

TLC (developing solvent, cyclohexane:ethyl acetate=2:1): Rf=0.50;

IR (liquid film): $\nu$=1740, 1600, 1585, 1250, 1040, 980, 875 cm$^{-1}$;

NMR (CDCl$_3$ solution): δ=7.52–6.70 (4H, m), 6.00–5.50 (2H, m), 5.10–3.30 (1H, m).

(f) (13E)-(5RS,6RS,9α,11α,15RS,16RS)-5-Bromo-6,9-epoxy-11,15-bis(tetrahydropyran-2-yloxy)-16-cyclopentyl-18,19,20-trinorprost-13-enoic acid methyl ester, having the following physical characteristic, was prepared from (5Z,13E)-(9α,11α,15RS,16RS)-9-hydroxy-11,15-bis(tetrahydropyran-2-yloxy)-16-cyclopentyl-18,19,20-trinorprosta-5,13-dienoic acid methyl ester.

TLC (developing solvent, cyclohexane:ethyl acetate=2:1): Rf=0.56.

(g) (13E)-(5RS,6RS,9α,11α,15S)-5-Bromo-6,9-epoxy-11,15-bis(tetrahydropyran-2-yloxy)-15-cyclohexyl-16,17,18,19,20-pentanorprost-13-enoic acid methyl ester, having the following physical characteristic, was prepared from (5Z,13E)-(9α,11α,15S)-9-hydroxy-11,15-bis(tetrahydropyran-2-yloxy)-15-cyclohexyl-16,17,18,19,20-pentanorprosta-5,13-dienoic acid methyl ester.

TLC (developing solvent, cyclohexane:ethyl acetate=2:1): Rf=0.55.

(h) (13E)-(5RS,6RS,9α,11α,15RS,17S)-5-Bromo-6,9-epoxy-11,15-bis(tetrahydropyran-2-yloxy)-17,20-dimethylprost-13-enoic acid methyl ester, having the following physical characteristic, was prepared from (5Z,13E)-(9α,11α,15RS,17S)-9-hydroxy-11,15-bis(tetrahydropyran-2-yloxy)-17,20-dimethylprosta-5,13-dienoic acid methyl ester.

TLC (developing solvent, cyclohexane:ethyl acetate=2:1): Rf=0.59.

(i) (13E)-(5RS,6RS,9α,11α,15S,16R)-5-Bromo-6,9-epoxy-11,15-bis(tetrahydropyran-2-yloxy)-16-methylprost-13-enoic acid methyl ester, having the following physical characteristics, was prepared from (5Z,13E)-(9α,11α,15S,16R)-9-hydroxy-11,15-bis(tetrahydropyran-2-yloxy)-16-methylprosta-5,13-dienoic acid methyl ester.

TLC (developing solvent, benzene:ethyl acetate=4:1): Rf=0.38 and 0.46;

IR (liquid film): $\nu$=1750, 980 cm$^{-1}$;

NMR (CDCl$_3$ solution): δ=5.70–5.30 (2H, m), 4.60–4.39 (2H, m), 3.68 (3H, broad s), 1.04–0.74 (6H, m).

(j) (13E)-(5RS,6RS,9α,11α,15S)-5-Bromo-6,9-epoxy-11,15-bis(tetrahydropyran-2-yloxy)-15-(trans-4-ethylcyclohexyl)-16,17,18,19,20-pentanorprost-13-enoic acid methyl ester, having the following physical characteristics, was prepared from (5Z,13E)-(9α,11α,15S)-9-hydroxy-11,15-bis(tetrahydropyran-2-yloxy)-15-(trans-4-ethylcyclohexyl)-16,17,18,19,20-pentanorprosta-B 5,13-dienoic acid methyl ester.

TLC (developing solvent, cyclohexane:ethyl acetate=2:1): Rf=0.42;

IR (liquid film): ν=1740, 1440, 975 cm$^{-1}$.

(k) (13E)-(5RS,6RS,9α,11α)-5-Bromo-6,9-epoxy-11,15-bis(tetrahydropyran-2-yloxy)-16,17,18,19,20-pentanorprost-13-enoic acid methyl ester, having the following physical characteristics, was prepared from (5Z,13E)-(9α,11α)-9-hydroxy-11,15-bis(tetrahydropyran-2-yloxy)-16,17,18,19,20-pentanorprosta-5,13-dienoic acid methyl ester [prepared as described in Reference Example 2].

TLC (developing solvent, benzene:ethyl acetate=2:1): Rf=0.64 and 0.68;

IR (liquid film): ν=1740, 980 cm$^{-1}$;

NMR (CDCl$_3$ solution): δ=5.76-5.52 (2H, m), 4.71-4.40 (3H, m), 3.66 (3H, s).

(l) (13E)-(5RS,6RS,9α,11α,15S)-5-Bromo-6,9-epoxy-11,15-bis(tetrahydropyran-2-yloxy)-16-cyclohexyl-17,18,19,20-tetranorprost-13-enoic acid methyl ester, having the following physical characteristics, was prepared from (5Z,13E)-(9α,11α,15S)-9-hydroxy-11,15-bis(tetrahydropyran-2-yloxy)-16-cyclohexyl-17,18,19,20-tetranorprosta-5,13-dienoic acid methyl ester.

IR (liquid film): ν=1740, 1445, 1205, 1140, 1080, 1040, 1025, 980 cm$^{-1}$;

NMR (CDCl$_3$ solution): δ=5.60-5.20 (2H, m), 4.70-4.30 (3H, m), 3.60 (3H, s), 4.30-3.20 (8H, m).

(m) (13E)-(5RS,6RS,9α,11α,15S)-5-Bromo-6,9-epoxy-11,15-bis(tetrahydropyran-2-yloxy)-17-cyclohexyl-18,19,20-trinorprost-13-enoic acid methyl ester, having the following physical characteristics, was prepared from (5Z,13E)-(9α,11α,15S)-9-hydroxy-11,15-bis(tetrahydropyran-2-yloxy)-17-cyclohexyl-18,19,20-trinorprosta-5,13-dienoic acid methyl ester.

TLC (developing solvent, benzene:ethyl acetate=2:1): Rf=0.70;

NMR (CDCl$_3$ solution): δ=5.67-5.16 (4H, m), 4.9-4.5 (2H, m), 4.3-3.0 (11H, m), 3.0-0.7 (38H, m).

EXAMPLE 2

(13E)-(5RS,6RS,9α,11α,15S)-5-Bromo-6,9-epoxy-11,15-dihydroxyprost-13-enoic acid methyl ester 360 mg of (13E)-(5RS,6RS,9α,11α,15S)-5-Bromo-6,9-epoxy-11,15-bis(tetrahydropyran-2-yloxy)prost-13-enoic acid methyl ester (prepared as described in Example 1) were dissolved in a mixture of 0.7 ml of tetrahydrofuran and 7 ml of 65% aqueous acetic acid and the mixture was stirred at 40° to 45° C. for one hour. The reaction mixture was then diluted with ethyl acetate, washed with water and an aqueous solution of sodium chloride, dried over magnesium sulphate and concentrated under reduced pressure. The residue was purified by column chromatography on silica gel using a mixture of cyclohexane and ethyl acetate (1:3) as eluent to give 210 mg of the title compound having the following physical characteristics:

TLC (developing solvent, ethyl acetate): Rf=0.20;

IR (liquid film): ν=3400, 1740, 1440, 975 cm$^{-1}$;

NMR (CDCl$_3$ solution): δ=5.64-5.38 (2H, m), 4.70-4.38 (1H, m), 4.30-3.75 (4H, m), 3.68 (3H, s), 1.01-0.78 (3H, m);

MASS: 428 (M+-18), 410 (M+-36), 384, 349 (428-79), 331, 305, 277.

The following compounds were obtained by the same procedure as described above.

(a) (13E)-(5RS,6RS,9α,11α,15S)-5-Bromo-6,9-epoxy-11,15-dihydroxyprost-13-enoic acid, having the following physical characteristics, was prepared from (13E)-(5RS,6RS,9α,11α,15S)-5-bromo-6,9-epoxy-11,15-bis(tetrahydropyran-2-yloxy)-prost-13-enoic acid [prepared as described in Example 1(a)]. TLC (developing solvent, ethyl acetate:formic acid=400:5): Rf=0.31;

IR (liquid film): ν=3400, 1710, 1440, 970 cm$^{-1}$;

NMR (CDCl$_3$ solution): δ=5.65-5.38 (2H, m), 4.96 (3H, broad s), 4.70-4.38 (1H, m), 4.30-3.70 (4H, m), 1.01-0.70 (3H, m).

(b) (13E)-(5RS,6RS,9α,11α,15S,16S)-5-Bromo-6,9-epoxy-11,15-dihydroxy-16-methylprost-13-enoic acid, having the following physical characteristics, was prepared from (13E)-(5RS,6RS, 9α,11α,15S,16S)-5-bromo-6,9-epoxy-11,15-bis(tetrahydropyran-2-yloxy)-16-methylprost-13-enoic acid [prepared as described in Example 1(b)].

TLC (developing solvent, chloroform:tetrahydrofuran:acetic acid=10:2:1): Rf=0.27 and 0.30;

IR (liquid film): ν=3400, 2995, 2940, 2880, 1715, 1380, 1245, 975 cm$^{-1}$;

NMR (CDCl$_3$ solution): δ=5.63-5.38 (2H, m), 5.63-5.15 (5H, m), 4.67-4.42 (1H, m) 1.00-0.69 (6H, m).

(c) (13E)-(5RS,6RS,9α,11α,15R)-5-Bromo-6,9-epoxy-11,15-dihydroxy-16,16-dimethylprost-13-enoic acid, having the following physical characteristics, was prepared from (13E)-(5RS,6RS,9α,11α,15R)-5-bromo-6,9-epoxy-11,15-bis(tetrahydropyran-2-yloxy)-16,16-dimethylprost-13-enoic acid [prepared as described in Example 1(c)].

TLC (developing solvent, chloroform:tetrahydrofuran:acetic acid=10:2:1): Rf=0.34 and 0.39;

IR (liquid film): ν=3400, 1715, 980 cm$^{-1}$;

NMR (CDCl$_3$ solution): δ=5.68-5.48 (2H, m), 4.68-4.40 (1H, m), 0.98-0.80 (9H, m).

(d) (13E)-(5RS,6RS,9α,11α,15R)-5-Bromo-6,9-epoxy-11,15-dihydroxy-16-(3-chlorophenoxy)-17,18,19,20-tetranorprost-13-enoic acid methyl ester, having the following physical characteristics, was prepared from (13E)-(5RS,6RS,9α,11α,15R)-5-bromo-6,9-epoxy-11,15-bis(tetrahydropyran-2-yloxy)-16-(3-chlorophenoxy)-17,18,19,20-tetranorprost-13-enoic acid methyl ester [prepared as described in Example 1(e)].

TLC (developing solvent, chloroform:tetrahydrofuran:acetic acid=10:2:1): Rf=0.35 and 0.39;

IR (liquid film): ν=3400, 1730, 1600, 1585, 1480, 1040, 975, 870 cm$^{-1}$;

NMR (CDCl$_3$ solution): δ=7.25-6.70 (4H, m), 5.76-5.60 (2H, m), 4.65-4.36 (2H, m), 4.30-3.70 (5H, m), 3.66 (3H, s).

(e) (13E)-(5RS,6RS,9α,11α,15S,16RS)-5-Bromo-6,9-epoxy-11,15-dihydroxy-16-cyclopentyl-18,19,20-trinorprost-13-enoic acid methyl ester, having the following physical characteristics, was prepared from (13E)-(5RS,6RS,9α,11α,15RS,16RS)-5-bromo-6,9-epoxy-11,15-bis(tetrahydropyran-2-yloxy)-16-cyclopentyl-18,19,20-trinorprost-13-enoic acid methyl ester [prepared as described in Example 1(f)].

TLC (developing solvent, chloroform:tetrahydrofuran:acetic acid=10:2:1): Rf=0.34 and 0.36; (15R-hydroxy isomer, Rf=0.42);

IR (liquid film): ν=3370, 1740, 1440, 1020, 980 cm$^{-1}$;

NMR (CDCl₃ solution): δ=5.55 (2H, m), 4.53 (1H, m), 4.30–3.70 (4H, m), 3.68 (3H, m), 0.88 (3H, m).

(f) (13E)-(5RS,6RS,9α,11α,15S)-5-Bromo-6,9-epoxy-11,15-dihydroxy-15-cyclohexyl-16,17,18,19,20-pentanorprost-13-enoic acid methyl ester, having the following physical characteristics, was prepared from (13E)-(5RS,6RS,9α,11α,15S)-5-bromo-6,9-epoxy-11,15-bis(tetrahydropyran-2-yloxy)-15-cyclohexyl-16,17,18,19,20-pentanorprost-13-enoic acid methyl ester [prepared as described in Example 1(g)].

TLC (developing solvent, chloroform:tetrahydrofuran:acetic acid=10:2:1): Rf=0.32;

IR (liquid film): ν=3500, 1730, 970 cm⁻¹;

NMR (CDCl₃ solution): δ=5.75–5.25 (2H, m), 4.7–4.35 (1H, m), 4.35–3.5 (4H, m), 3.66 (3H, s), 3.5–3.1 (2H, m).

(g) (13E)-(5RS,6RS,9α,11α,15S,17S)-5-Bromo-6,9-epoxy-11,15-dihydroxy-17,20-dimethylprost-13-enoic acid methyl ester, having the following physical characteristics, was prepared from (13E)-(5RS,6RS,9α,11α,15RS,17S)-5-bromo-6,9-epoxy-11,15-bis(tetrahydropyran-2-yloxy)-17,20-dimethylprost-13-enoic acid methyl ester [prepared as described in Example 1(h)].

TLC (developing solvent, chloroform:tetrahydrofuran:acetic acid=10:2:1): Rf=0.28 and 0.31; (15R-hydroxy isomer Rf=0.38);

IR (liquid film): ν=3350, 1740, 1440, 975 cm⁻¹;

NMR (CDCl₃ solution): δ=5.51 (2H, m), 4.50 (1H, m), 4.30–3.50 (4H, m), 3.67 (3H, s), 0.90 (6H, m).

(h) (13E)-(5RS,6RS,9α,11α,15S,16R)-5-Bromo-6,9-epoxy-11,15-dihydroxy-16-methylprost-13-enoic acid methyl ester, having the following physical characteristics, was prepared from (13E)-(5RS,6RS,9α,11α,15S,16R)-5-bromo-6,9-epoxy-11,15-bis-(tetrahydropyran-2-yloxy)-16-methylprost-13-enoic acid methyl ester [prepared aas described in Example 1(i)].

TLC (developing solvent, ethyl acetate:chloroform=3:1): Rf=0.44;

IR (liquid film): ν=3400, 1740, 980 cm⁻¹;

NMR (CDCl₃ solution): δ=5.65–5.44 (2H, m), 4.63–4.40 (1H, m), 3.66 (3H, s), 1.00–0.78 (6H, m).

(i) (13E)-(5RS,6RS,9α,11α,15S)-5-Bromo-6,9-epoxy-11,15-dihydroxy-15-(trans-4-ethylcyclohexyl)-16,17,18,19,20-pentanorprost-13-enoic acid methyl ester, having the following physical characteristics, was prepared from (13E)-(5RS,6RS, 9α,11α,15S)-5-bromo-6,9-epoxy-11,15-bis(tetrahydropyran-2-yloxy)-15-(trans-4-ethylcyclohexyl)-16,17,18,19,20-pentanorprost-13-enoic acid methyl ester [prepared as described in Example 1(j)].

TLC (developing solvent, chloroform:tetrahydrofuran:acetic acid=10:2:1): Rf=0.3;

IR (liquid film): ν=3400, 1740, 1440, 970 cm⁻¹;

NMR (CDCl₃ solution): δ=5.8–5.4 (2H, m), 3.67 (3H, s), 4.65–3.5 (5H, m), 1.1–0.6 (3H, m).

(j) (13E)-(5RS,6RS,9α,11α)-5-Bromo-6,9-epoxy-11,15-dihydroxy-16,17,18,19,20-pentanorprost-13-enoic acid methyl ester, having the following physical characteristics, was prepared from (13E)-(5RS,6RS,9α,11α)-5-bromo-6,9-epoxy-11,15-bis(tetrahydropyran-2-yloxy)-16,17,18,19,20-pentanorprost-13-enoic acid methyl ester [prepared as described in Example 1(k)].

TLC (developing solvent, chloroform:ethyl acetate=3:1, twice development): Rf=0.25 and 0.30;

IR (liquid film): ν=3400, 1740, 980 cm⁻¹;

NMR (CDCl₃ solution): δ=5.79–5.54 (2H, m), 4.63–4.36 (1H, m), 4.10 (2H, s), 3.67 (3H, s).

(k) (13E)-(5RS,6RS,9α,11α,15S)-5-Bromo-6,9-epoxy-11,15-dihydroxy-16-cyclohexyl-17,18,19,20-tetranorprost-13-enoic acid methyl ester, having the following physical characeristics, was prepared from (13E)-(5RS,6RS,9α,11α,15S)-5-bromo-6,9-epoxy-11,15-bis(tetrahydropyran-2-yloxy)-16-cyclohexyl-17,18,19,20-tetranorprost-13-enoic acid methyl ester [prepared as described in Example 1(l)].

TLC (developing solvent, chloroform:tetrahydrofuran:acetic acid=10:2:1): Rf=0.33 and 0.38;

IR (liquid film): ν=3400, 1740, 1450, 1080, 1060, 975 cm⁻¹;

NMR (CDCl₃ solution): δ=5.58–5.40 (2H, m), 4.60–4.40 (1H, m), 4.30–3.55 (4H, m), 3.67 (3H, s), 3.54–3.00 (2H, broad s).

(l) (13E)-(5RS,6RS,9α,11α,15S)-5-bromo-6,9-epoxy-11,15-dihydroxy-17-cyclohexyl-18,19,20-trinorprost-13-enoic acid methyl ester, having the following physical characteristics, was prepared from (13E)-(5RS,6RS,9α,11α,15S)-5-bromo-6,9-epoxy-11,15-bis(tetrahydropyran-2-yloxy)-17-cyclohexyl-18,19,20-trinorprost-13-enoic acid methyl ester [prepared as described in Example 1(m)].

TLC (developing solvent, chloroform:tetrahydrofuran:acetic acid=10:2:1): Rf=0.22 and 0.28;

IR (liquid film): ν=3400, 3000, 2950, 2870, 1750, 1450, 1380, 1250, 1200, 1180, 1070, 980 cm⁻¹;

NMR (CDCl₃ solution): δ=5.65–5.4 (2H, m), 4.8–4.3 (1H, m), 4.3–3.2 (4H, m), 3.67 (3H, s), 2.7–0.7 (29H, m).

EXAMPLE 3

(13E)-(5RS,6RS,9α,11α,15R)-5-Bromo-6,9-epoxy-11,15-dihydroxy-16,16-dimethylprost-13-enoic acid methyl ester By proceeding as described in Example 1 but using 800 mg of N-bromosuccinimide and 1.47 g of (5Z,13E)-(9α,11α,15R)-9,11,15-trihydroxy-16,16-dimethylprosta-5,13-dienoic acid methyl ester dissolved in a mixture of 40 ml of chloroform and 4 ml of tetrahydrofuran, there was obtained 1.24 g of the title compound having the following physical characteristics:

TLC (developing solvent, chloroform:tetrahydrofuran:acetic acid=10:2:1): Rf=0.52;

IR (liquid film): ν=3400, 1730, 975 cm⁻¹;

NMR (CDCl₃ solution): δ=5.8–5.3 (2H, m), 3.66 (3H, s), 4.35–3.4 (4H, m), 3.3–2.6 (2H, m), 0.88 (3H, broad s), 0.83 (3H, broad s).

The following compounds were prepared by the same procedure as described above.

(a) (13E)-(5RS,6RS,9α,11α,15S)-5-Bromo-6,9-epoxy-11,15-dihydroxy-15-(3-propylcyclopentyl)-16,17,18,19,20-pentanorprost-13-enoic acid methyl ester, having the following physical characteristics, was prepared from (5Z,13E)-(9α,11α,15S)-9,11,15-trihydroxy-15-(3-propylcyclopentyl)-16,17,18,19,20-pentanorprost-13-enoic acid methyl ester.

TLC (developing solvent, chloroform:tetrahydrofuran:acetic acid=10:2:1): Rf=0.48;

IR (liquid film): ν=3400, 1735, 970 cm⁻¹;

NMR (CDCl₃ solution): δ=5.65–5.4 (2H, m), 4.65–4.35 (1H, m), 3.67 (3H, s), 4.35–3.45 (4H, m), 3.3–2.7 (2H, m).

(b) (13E)-(5RS,6RS,9α,11α,15RS)-5-Bromo-6,9-epoxy-11,15-dihydroxy-15-methylprost-13-enoic acid methyl ester, having the following physical characteristics, was prepared from (5Z,13E)-(9α,11α,15RS)-

9,11,15-trihydroxy-15-methylprosta-5,13-dienoic acid methyl ester.

TLC (developing solvent, chloroform:tetrahydrofuran:acetic acid = 10:2:1): Rf=0.43;

IR (liquid film): ν=3400, 1715, 980 cm⁻¹;

NMR (CDCl₃ solution): δ=5.8–5.4 (2H, m), 4.65–4.35 (1H, m), 4.3–3.5 (3H, m), 3.66 (3H, s), 3.4–2.8 (2H, m), 1.27 (3H, s).

(c) (13E)-(5RS,6RS,9α,11α,15R)-5-Bromo-6,9-epoxy-11,15-dihydroxy-15-(1-butylcyclobutyl)-16,17,18,19,20-pentanorprost-13-enoic acid methyl ester, having the following physical characteristics, was prepared from (5Z,13E)-(9α,11α,15R)-9,11,15-trihydroxy-15-(1-butylcyclobutyl)-16,17,18,19,20-pentanorprosta-5,13-dienoic acid methyl ester.

TLC (developing solvent, diethyl ether:benzene:tetrahydrofuran=1:1:1): Rf=0.69;

IR (liquid film): ν=3400, 1730, 1430, 1370, 1240, 1050, 970 cm⁻¹;

NMR (CDCl₃ solution): δ=5.65–5.50 (2H, m), 4.63–4.40 (1H, m), 4.30–3.75 (2H, m), 3.67 (3H, s), 0.91 (3H, t).

EXAMPLE 4

(5RS,6RS,9α,11α,15S)-5-Bromo-6,9-epoxy-11,15-dihydroxyprostanoic acid methyl ester 350 mg of (13E)-(5RS,6RS,9α,11α,15S)-5-bromo-6,9-epoxy-11,15-dihydroxyprost-13-enoic acid methyl ester (prepared as described in Example 2) were hydrogenated at a pressure of one atmosphere in 6 ml of ethanol containing 120 mg of 5% palladium on charcoal at room temperature. The reduction was stopped after the absorption of one equivalent of hydrogen. The catalyst was removed by filtration and the filtrate was concentrated under reduced pressure. The residue was purified by column chromatography on silica gel using a mixture of cyclohexane and ethyl acetate (1:1) as eluent to give 210 mg of the title compound having the following physical characteristics:

TLC (developing solvent, ethyl acetate): Rf=0.44;

IR (liquid film): ν=3400, 1740, 1440, 1200 cm⁻¹;

NMR (CDCl₃ solution): δ=4.52 (1H, m), 4.20 (1H, m), 3.97 (1H, m), 3.85–3.50 (2H, m), 3.67 (3H, s), 1.03–0.77 (3H, m).

EXAMPLE 5

(13E)-(6RS,9α,11α,15S)-6,9-Epoxy-11,15-bis(tetrahydropyran-2-yloxy)prost-13-enoic acid methyl ester In a Pyrex (registered Trade Mark) vessel, a solution of 540 mg of (13E)-(5RS,6RS,9α,11α,15S)-5-bromo-6,9-epoxy-11,15-bis(tetrahydropyran-2-yloxy)prost-13-enoic acid methyl ester (prepared as described in Example 1), 322 mg of tri-n-butyl-tinhydride and 24 mg of 2,2'-azobisisobutyronitrile in 6 ml of benzene was irradiated with light from a high pressure mercury lamp at room temperature for 30 minutes. To the reaction mixture was added an aqueous sodium carbonate solution and the mixture was extracted with ethyl acetate. The extract was washed with water and aqueous sodium chloride solution, dried over magnesium sulphate and concentrated under reduced pressure. The residue was purified by column chromatography on silica gel using a mixture of cyclohexane and ethyl acetate (4:1) as eluent to give 435 mg of the title compound having the following physical characteristics:

TLC (developing solvent, benzene:ethyl acetate=2:1): Rf=0.50;

IR (liquid film): ν=1740, 1440, 1200, 1020, 980 cm⁻¹;

NMR (CDCl₃ solution): δ=5.73–5.26 (2H, m), 4.81–4.57 (2H, m), 4.55–4.30 (1H, m), 4.25–3.26 (10H, m), 1.00–0.75 (3H, m);

MASS: 505 (M⁺-31), 452, 434, 421, 403, 381, 350, 332, 306.

The following compounds were prepared by the same procedure as described above.

(a) (13E)-(6RS,9α,11α,15S)-6,9-Epoxy-11,15-bis(tetrahydropyran-2-yloxy)prost-13-enoic acid, having the following physical characteristics, was prepared from (13E)-(5RS,6RS,9α,11α,15S)-5-bromo-6,9-epoxy-11,15-bis(tetrahydropyran-2-yloxy)prost-13-enoic acid [prepared as described in Example 1(a)].

TLC (developing solvent, methylene chloride:methanol=20:1): Rf=0.15;

IR (liquid film): ν=1710, 1440, 1020, 980 cm⁻¹;

NMR (CDCl₃ solution): δ=8.80 (1H, broad s), 5.70–5.25 (2H, m), 4.80–4.60 (2H, m), 4.55–4.26 (1H, m), 4.23–3.25 (7H, m), 1.02–0.70 (3H, m).

(b) (13E)-(6RS,9α,11α,15S,16S)-6,9-Epoxy-11,15-bis(tetrahydropyran-2-yloxy)-16-methylprost-13-enoic acid, having the following physical characteristics, was prepared from (13E)-(5RS,6RS,9α,11α,15S,16S)-5-bromo-6,9-epoxy-11,15-bis(tetrahydropyran-2-yloxy)-16-methylprost-13-enoic acid [prepared as described in Example 1(b)].

IR (liquid film): ν=1710, 1440, 1020, 980 cm⁻¹;

NMR (CDCl₃ solution): δ=8.70 (1H, broad s), 5.70–5.25 (2H, m), 4.80–4.60 (2H, m), 4.55–4.26 (1H, m), 4.23–3.25 (7H, m), 1.02–0.75 (6H, m).

(c) (13E)-(6RS,9α,11α,15R)-6,9-Epoxy-11,15-bis(tetrahydropyran-2-yloxy)-16,16-dimethylprost-13-enoic acid, having the following physical characteristics, was prepared from (13E)-(5RS,6RS,9α,11α,15R)-5-bromo-6,9-epoxy-11,15-bis(tetrahydropyran-2-yloxy)-16,16-dimethylprost-13-enoic acid [prepared as described in Example 1(c)].

IR (liquid film): ν=1710, 1440, 1020, 980 cm⁻¹;

NMR (CDCl₃ solution): δ=8.80 (1H, broad s), 5.70–5.25 (2H, m), 4.80–4.60 (2H, m), 4.55–4.26 (1H, m), 4.23–3.25 (7H, m), 1.02–0.70 (9H, m).

(d) (13E)-(6RS,9α,11α,15R)-6,9-Epoxy-11,15-bis(tetrahydropyran-2-yloxy)-16-phenoxy-17,18,19,20-tetranorprost-13-enoic acid, having the following physical characteristics, was prepared from (13E)-(5RS,6RS,9α,11α,15R)-5-bromo-6,9-epoxy-11,15-bis(tetrahydropyran-2-yloxy)-16-phenoxy-17,18,19,20-tetranorprost-13-enoic acid [prepared as described in Example 1(d)].

IR (liquid film): ν=1710, 1600, 1590, 1500, 1440, 1250, 980, 760 cm⁻¹;

NMR (CDCl₃ solution): δ=8.60 (1H, broad s), 7.40–6.80 (5H, m), 5.76–5.30 (2H, m), 4.80–4.25 (4H, m), 4.22–3.25 (8H, m).

EXAMPLE 6

(13E)-(5RS,6RS,9α,11α,15S)-5-Phenylseleno-6,9-epoxy-11,15-bis(tetrahydropyran-2-yloxy)prost-13-enoic acid methyl ester (a) Under an atmosphere of nitrogen, 63 mg of sodium borohydride were added all at once to a solution of 296 mg of diphenyldiselenide in 6 ml of absolute ethanol at 0° to 5° C., and the mixture was stirred for 30 minutes. To the reaction mixture thus obtained was added a solution of 710 mg of (13E)-(5RS,6RS,9α,11α,15S)-5-bromo-6,9-epoxy-11,15-bis(tetrahydropyran- 2-yloxy)prost-13-enoic acid methyl ester (prepared as described in Example 1) in 3 ml of ethanol and the mixture was then stirred at 65° to 70° C. for 2 hours. Afterwards the reaction mixture was concentrated under reduced pressure. To the residue was added an aqueous solution of ammonium chloride and the mixture was extracted with ethyl acetate. The extract was washed with water and an aqueous solution of sodium chloride, dried over magnesium sulphate and concentrated under reduced pressure. The residue was purified by column chromatography on silica gel using a mixture of benzene and ethyl acetate (7:1) as eluent to give 560 mg of the title compound having the following physical characteristics:

TLC (developing solvent, benzene:ethyl acetate=4:1): Rf=0.46 and 0.50;

IR (Liquid film): $\nu$=1740, 1580, 1440, 1130, 1020, 980, 790 cm$^{-1}$;

NMR (CCl$_4$ solution): $\delta$=7.80–7.00 (5H, m), 5.75–5.20 (2H, m), 3.62 (3H, s).

(b) To a solution of 3.3 g of (5Z,13E)-(9α,11α,15S)-9-hydroxy-11,15-bis(tetrahydropyran-2-yloxy)prosta-5,13-dienoic acid methyl ester in 60 ml of tetrahydrofuran was added 610 mg of calcium carbonate at −20° C., and then 6 ml of a solution of benzeneselenenyl bromide in tetrahydrofuran (prepared by adding 0.19 ml of bromine to a solution of 1.25 g of diphenyldiselenide in 6 ml of tetrahydrofuran and stirring the mixture at room temperature for one hour) was added and the reaction mixture was stirred at the same temperature for 10 minutes and further stirred for one hour at 0° C., and then an aqueous solution of ammonium chloride was added. The reaction mixture was extracted with ethyl acetate. The extract was washed with water and an aqueous solution of sodium chloride, dried over magnesium sulphate and concentrated under reduced pressure. The residue was purified by column chromatography on silica gel using a mixture of cyclohexane and ethyl acetate (7:1) as eluent to give 1.62 g of the title compound having the same physical characteristics as hereinbefore described.

EXAMPLE 7

(4E,13E)-(6RS,9α,11α,15S)-6,9-Epoxy-11,15-bis(tetrahydropyran-2-yloxy)prosta-4,13-dienoic acid methyl ester To a solution of 560 mg of (13E)-(5RS,6RS,9α,11α,15S)-5-phenylseleno-6,9-epoxy-11,15-bis(tetrahydropyran-2-yloxy)prost-13-enoic acid methyl ester (prepared as described in Example 6) in a mixture of 6 ml of ethyl acetate and 3 ml of tetrahydrofuran was added 0.5 ml of 30% hydrogen peroxide and 100 mg of sodium bicarbonate, and the reaction mixture was then stirred for one hour. Afterwards it was extracted with ethyl acetate. The extract was washed with an aqueous solution of sodium carbonate, water and an aqueous solution of sodium chloride, dried over magnesium sulphate and concentrated under reduced pressure. The residue was purified by column chromatography on silica gel using a mixture of benzene and ethyl acetate (6:1) as eluent to give 380 mg of the title compound having the following physical characteristics:

TLC (developing solvent, benzene:ethyl acetate=4:1): Rf=0.37 and 0.41;

IR (liquid film): $\nu$=1740, 1440, 1200, 1020, 980 cm$^{-1}$;

NMR (CDCl$_3$ solution): $\delta$=5.85–5.30 (4H, m), 4.81–3.26 (13H, m), 1.00–0.75 (3H, m).

EXAMPLE 8

(4E,13E)-(6RS,9α,11α,15S)-6,9-Epoxy-11,15-bis(tetrahydropyran-2-yloxy)prosta-4,13-dienoic acid To a solution of 480 mg of (4E,13E)-(6RS,9α,11α,15S)-6,9-epoxy-11,15-bis(tetrahydropyran-2-yloxy)prosta-4,13-dienoic acid methyl ester (prepared as described in Example 7) in 3 ml of methanol was added 5 ml of a 5% aqueous solution of potassium hydroxide at 45° to 50° C., and the mixture was stirred for one hour at the same temperature. The reaction mixture was then acidified to pH 5 to 6 with an aqueous solution of oxalic acid and extracted with ethyl acetate. The extract was washed with water and an aqueous solution of sodium chloride, dried over magnesium sulphate and concentrated under reduced pressure. The residue was purified by column chromatography on silica gel using a mixture of cyclohexane and ethanol (20:1) as eluent to give 460 mg of the title compound having the following physical characteristics:

TLC (developing solvent, methylene chloride:methanol=20:1): Rf=0.19;

IR (liquid film): $\nu$=1740, 1710, 1440, 1200, 1130, 1020, 980 cm$^{-1}$;

NMR (CDCl$_3$ solution): $\delta$=9.80–9.40 (1H, m), 5.85–5.15 (4H, m), 4.82–3.27 (10H, m), 1.02–0.75 (3H, m).

The following compounds were prepared by the same procedure as described above.

(a) (13E)-(6RS,9α,11α,15S)-6,9-Epoxy-11,15-bis(tetrahydropyran-2-yloxy)prost-13-enoic acid, having the same physical characteristics as described in Example 5(a), was prepared from its methyl ester (prepared as described in Example 5).

(b) (13E)-(6RS,9α,11α,15S,16R)-6,9-Epoxy-11,15-dihydroxy-16-methylprost-13-enoic acid, having the following physical characteristics, was prepared from its methyl ester [prepared as described in Example 10(d) hereafter].

TLC (developing solvent, ethyl acetate): Rf=0.42;

IR (liquid film): $\nu$=3400, 1715, 980 cm$^{-1}$;

NMR (CDCl$_3$ solution): $\delta$=5.61–5.10 (5H, m), 4.55–4.28 (1H, m), 4.00–3.50 (3H, m), 1.01–0.70 (6H, m).

EXAMPLE 9

(13E)-(6RS,9α,11α,15S)-6,9-Epoxy-11,15-dihydroxyprost-13-enoic acid methyl ester By proceeding as described in Example 2 but using 435 mg of (13E)-(6RS,9α,11α,15S)-6,9-epoxy-11,15-bis(tetrahydropyran-2-yloxy)prost-13-enoic acid methyl ester (prepared as described in Example 5) dissolved in a mixture of 0.7 ml of tetrahydrofuran and 9 ml of 65% aqueous acetic acid, there were obtained 220 mg of the title compound having the following physical characteristics:

TLC (developing solvent, ethyl acetate): Rf=0.14 and 0.17;

IR (liquid film): $\nu$=3400, 1740, 1440, 980 cm$^{-1}$;

NMR (CDCl$_3$ solution): $\delta$=5.62–5.43 (2H, m), 4.60–3.75 (4H, m), 3.67 (3H, s), 1.00–0.76 (3H, m);

MASS: 350 (M$^+$-18), 332 (M$^+$-36), 306, 278, 99.

The following compounds were prepared by the same procedure as described above.

(a) (13E)-(6RS,9α,11α,15S)-6,9-Epoxy-11,15-dihydroxyprost-13-enoic acid, having the following physical characteristics, was prepared from (13E)-(6RS,9α,11α,15S)-6,9-epoxy-11,15-bis(tetrahydropyran-2-yloxy)- prost-13-enoic acid [prepared as described in Example 5(a) or 8(a)].

TLC (developing solvent, benzene:dioxane:acetic acid=20:10:1): Rf=0.16 and 0.19;

IR (liquid film): ν=3400, 1710, 1410, 980 cm$^{-1}$;

NMR (CDCl$_3$ solution): δ=5.66–5.43 (2H, m), 4.98 (3H, broad s), 4.57–4.26 (1H, m), 4.15–3.75 (3H, m), 1.02–0.70 (3H, m).

(b) (13E)-(6RS,9α,11α,15S,16S)-6,9-Epoxy-11,15-dihydroxy-16-methylprost-13-enoic acid, having the following physical characteristics, was prepared from (13E)-(6RS,9α,11α,15S,16S)-6,9-epoxy-11,15-bis(tetrahydropyran-2-yloxy)-16-methylprost-13-enoic acid [prepared as described in Example 5(b)].

TLC (developing solvent, chloroform:tetrahydrofuran:acetic acid=10:2:1): Rf=0.25;

IR (liquid film): ν=3400, 1710, 1410, 980 cm$^{-1}$;

NMR (CDCl$_3$ solution): δ=5.66–5.43 (2H, m), 5.01 (3H, broad s), 4.57–4.26 (1H, m), 4.15–3.80 (3H, m), 1.02–0.75 (6H, m).

(c) (13E)-(6RS,9α,11α,15R)-6,9-Epoxy-11,15-dihydroxy-16,16-dimethylprost-13-enoic acid, having the following physical characteristics, was prepared from (13E)-(6RS,9α,11α,15R)-6,9-epoxy-11,15-bis(tetrahydropyran-2-yloxy)-16,16-dimethylprost-13-enoic acid [prepared as described in Example 5(c)].

TLC (developing solvent, chloroform:tetrahydrofuran:acetic acid=10:2:1): Rf=0.27;

IR (liquid film): ν=3400, 1710, 1410, 980 cm$^{-1}$;

NMR (CDCl$_3$ solution): δ=5.70–5.40 (2H, m), 4.90 (3H, broad s), 4.57–4.26 (1H, m), 4.10–3.70 (3H, m), 1.02–0.70 (9H, m).

(d) (13E)-(6RS,9α,11α,15R)-6,9-Epoxy-11,15-dihydroxy-16-phenoxy-17,18,19,20-tetranorprost-13-enoic acid, having the following physical characteristics, was prepared from (13E)-(6RS,9α,11α,15R)-6,9-epoxy-11,15-bis(tetrahydropyran-2-yloxy)-16-phenoxy-17,18,19,20-tetranorprost-13-enoic acid [prepared as described in Example 5(d)].

IR (liquid film): ν=3400, 1710, 1600, 1590, 1500, 1250, 980, 760 cm$^{-1}$;

NMR (CDCl$_3$ solution): δ=7.40–6.80 (5H, m), 5.76–5.55 (2H, m), 5.01 (3H, broad s), 4.65–4.25 (2H, m), 4.15–3.80 (4H, m).

(e) (4E,13E)-(6RS,9α,11α,15S)-6,9-Epoxy-11,15-dihydroxyprosta-4,13-dienoic acid methyl ester, having the following physical characteristics, was prepared from (4E,13E)-(6RS,9α,11α,15S)-6,9-epoxy-11,15-bis(tetrahydropyran-2-yloxy)-prosta-4,13-dienoic acid methyl ester [prepared as described in Example 7].

TLC (developing solvent, ethyl acetate, twice development): Rf=0.21;

IR (liquid film): ν=3400, 1740, 1440, 1050, 975 cm$^{-1}$;

NMR (CDCl$_3$ solution): δ=5.85–5.30 (4H, m), 4.62–3.78 (4H, m), 3.68 (3H, s), 1.02–0.75 (3H, m).

(f) (4E,13E)-(6RS,9α,11α,15S)-6,9-Epoxy-11,15-dihydroxyprosta-4,13-dienoic acid, having the following physical characteristics, was prepared from (4E,13E)-(6RS,9α,11α,15S)-6,9-epoxy-11,15-bis(tetrahydropyran-2-yloxy)prosta-4,13-dienoic acid (prepared as described in Example 8). m.p.: 80°–85° C.;

TLC (developing solvent, benzene:dioxane:acetic acid=20:10:1): Rf=0.16 and 0.19;

IR(KBr tablet): ν=3400, 1705, 1170, 1060, 975 cm$^{-1}$;

NMR (CDCl$_3$ solution): δ=6.10–5.20 (7H, m), 4.68–3.53 (4H, m), 1.03–0.72 (3H, m).

EXAMPLE 10

(13E)-(6RS,9α,11α,15R)-6,9-Epoxy-11,15-dihydroxy-16-(3-chlorophenoxy)-17,18,19,20-tetranorprost-13-enoic acid methyl ester By proceeding as described in Example 5 but using 110 mg of (13E)-(5RS,6RS,9α,11α,15R)-5-bromo-6,9-epoxy-11,15-dihydroxy-16-(3-chlorophenoxy)-17,18,19,20-tetranorprost-13-enoic acid methyl ester [prepared as described in Example 2(d)], 69 mg of tri-n-butyltinhydride and 5.6 mg of 2,2'-azobisisobutyronitrile dissolved in 1.8 ml of benzene, there were obtained 88 mg of the title compound having the following physical characteristics.

TLC (developing solvent, ethyl acetate): Rf=0.34;

IR (liquid film): ν=3400, 1740, 1600, 1585, 1480, 1240, 1040, 980 cm$^{-1}$;

NMR (CDCl$_3$ solution): δ=7.20–6.70 (4H, m), 5.78–5.60 (2H, m), 4.57–4.30 (2H, m), 4.05–3.70 (4H, m).

The following compounds were prepared by the same procedure as described above.

(a) (13E)-(6RS,9α,11α,15S,16RS)-6,9-Epoxy-11,15-dihydroxy-16-cyclopentyl-18,19,20-trinorprost-13-enoic acid methyl ester, having the following physical characteristics, was prepared from (13E)-(5RS,6RS,9α,11α,15S,16RS)-5-bromo-6,9-epoxy-11,15-dihydroxy-16-cyclopentyl-18,19,20-trinorprost-13-enoic acid methyl ester [prepared as described in Example 2(e)].

TLC (developing solvent, ethyl acetate): Rf=0.37;

IR (liquid film): ν=3400, 1740, 1440, 1020, 975 cm$^{-1}$;

NMR (CDCl$_3$ solution): δ=5.55 (2H, m), 4.43 (1H, m), 4.20–3.60 (3H, m), 3.66 (3H, s), 0.88 (3H, m).

(b) (13E)-(6RS,9α,11α,15S)-6,9-Epoxy-11,15-dihydroxy-15-cyclohexyl-16,17,18,19,20-pentanorprost-13-enoic acid methyl ester, having the following physical characteristics, was prepared from (13E)-(5RS,6RS,9α,11α,15S)-5-bromo-6,9-epoxy-11,15-dihydroxy-15-cyclohexyl-16,17,18,19,20-pentanorprost-13-enoic acid methyl ester [prepared as described in Example 2(f)].

TLC (developing solvent, ethyl acetate): Rf=0.29;

IR (liquid film): ν=3400, 1740, 975 cm$^{-1}$;

NMR (CDCl$_3$ solution): δ=5.6–5.4 (2H, m), 4.6–4.3 (1H, m), 4.2–3.5 (3H, m), 3.67 (3H, s), 3.2–2.6 (2H, m).

(c) (13E)-(6RS,9α,11α,15S,17S)-6,9-Epoxy-11,15-dihydroxy-17,20-dimethylprost-13-enoic acid methyl ester, having the following physical characteristics, was prepared from (13E)-(5RS,6RS,9α,11α,15S,17S)-5-bromo-6,9-epoxy-11,15-dihydroxy-17,20-dimethylprost-13-enoic acid methyl ester [prepared as described in Example 2(g)].

TLC (developing solvent, ethyl acetate): Rf=0.30;

IR (liquid film): ν=3400, 1740, 1440, 1015, 975 cm$^{-1}$;

NMR (CDCl$_3$ solution): δ=5.50 (2H, m), 4.42 (1H, m), 4.28–3.60 (3H, m), 3.67 (3H, s), 0.90 (6H, m).

(d) (13E)-(6RS,9α,11α,15S,16R)-6,9-Epoxy-11,15-dihydroxy-16-methylprost-13-enoic acid methyl ester, having the following physical characteristics, was prepared from (13E)-(5RS,6RS,9α,11α,15S,16R)-5-bromo-6,9-epoxy-11,15-dihydroxy-16-methylprost-13-enoic acid methyl ester [prepared as described in Example 2(h)].

TLC (developing solvent, benzene:ethyl acetate=1:4): Rf=0.54;

IR (liquid film): ν=3400, 1740, 980 cm$^{-1}$;

NMR (CDCl$_3$ solution): δ=5.63j–5.40 (2H, m), 4.61–4.31 (1H, m), 3.67 (3H, s), 1.03–0.72 (6H, m).

(e) (13E)-(6RS,9α,11α,15R)-6,9-Epoxy-11,15-dihydroxy-16,16-dimethylprost-13-enoic acid methyl ester, having the following physical characteristics, was prepared from (13E):(5RS,6RS,9α,11α,15R)-5-bromo-6,9-epoxy-11,15-dihydroxy-16,16-dimethylprost-13-enoic acid methyl ester (prepared as described in Example 3).

TLC (developing solvent, ethyl acetate): Rf=0.52;
IR (liquid film): ν=3400, 1740, 975 cm$^{-1}$;
NMR (CDCl$_3$ solution): δ=5.8–5.3 (2H, m), 4.55–4.25 (1H, m), 3.64 (3H, s), 4.1–3.5 (3H, m), 1.0–0.7 (6H, m).

(f) (13E)-(6RS,9α,11α,15S)-6,9-Epoxy-11,15-dihydroxy-15-(3-propylcyclopentyl)-16,17,18,19,20-pentanorprost-13-enoic acid methyl ester, having the following physical characteristics, was prepared from (13E)-(5RS,6RS,9α, 11α,15S)-5-bromo-6,9-epoxy-11,15-dihydroxy-15-(3-propylcyclopentyl)-16,17,18,19,20-pentanorprost-13-enoic acid methyl ester [prepared as described in Example 3(a)].

TLC (developing solvent, ethyl acetate): Rf=0.20;
IR (chloroform solution): ν=3400, 1730, 970 cm$^{-1}$;
NMR (CDCl$_3$ solution): δ=5.6–5.4 (2H, m), 4.16–4.3 (1H, m), 3.66 (3H, s), 4.1–3.4 (3H, m).

(g) (13E)-(6RS,9α,11α,15RS)-6,9-Epoxy-11,15-dihydroxy-15-methylprost-13-enoic acid methyl ester, having the following physical characteristics, was prepared from (13E)-(5RS,6RS, 9α,11α,15RS)-5-bromo-6,9-epoxy-11,15-dihydroxy-15-methylprost-13-enoic acid methyl ester [prepared as described in Example 3(b)].

TLC (developing solvent, ethyl acetate): Rf=0.4;
IR (liquid film): ν=3400, 1740, 980 cm$^{-1}$;
NMR (CDCL$_3$ solution): δ=5.8–5.3 (2H, m), 4.8–4.3 (1H, m), 4.1–3.5 (2H, m), 3.65 (3H, s), 1.27 (3H, s).

(h) (13E)-(6RS,9α,11α,15S)-6,9-Epoxy-11,15-dihydroxy-16-cyclohexyl-17,18,19,20-tetranorprost-13-enoic acid methyl ester, having the following physical characteristics, was prepared from (13E)-(5RS,6RS,9α,11α,15S)-5-bromo-6,9-epoxy-11,15-dihydroxy-16-cyclohexyl-17,18,19,20-tetranorprost-13-enoic acid methyl ester [prepared as described in Example 2(k)].

TLC (developing solvent, cyclohexane:ethyl acetate=1:2):
Rf=0.11 and 0.13;
IR (liquid film): ν=3350, 1730, 1440, 1180, 1070, 980 cm$^{-1}$;
NMR (CDCl$_3$ solution): δ=5.57–5.35 (2H, m), 4.55–4.28 (1H, m), 4.28–3.45 (3H, m), 3.65 (3H, s).

(i) (13E)-(6RS,9α,11α,15S)-6,9-Epoxy-11,15-dihydroxy-17-cyclohexyl-18,19,20-trinorprost-13-enoic acid methyl ester, having the following physical characteristics, was prepared from (13E)-(5RS,6RS,9α,11α,15S)-5-bromo-6,9-epoxy-11,15-dihydroxy-17-cyclohexyl-18,19,20-trinorprost-13-enoic acid methyl ester [prepared as described in Example 2(1)].

TLC (developing solvent, ethyl acetate): Rf=0.47 and 0.39;
IR (liquid film): ν=3450, 2930, 2850, 1740, 1450, 1250, 1050, 970, 730 cm$^{-1}$;
NMR (CDCl$_3$ solution): δ=5.7–5.4 (2H, m), 4.6–4.3 (1H, m), 4.2–3.5 (3H, m), 3.67 (3H, s), 2.7–0.7 (31H, m).

The present invention includes within its scope pharmaceutical compositions which comprise at least one new therapeutically useful compound of general formula II, or cyclodextrin clathrate or non-toxic salt thereof, together with a pharmaceutical carrier or coating. In clinical practice the new compounds of the present invention will normally be administered orally, vaginally, rectally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, lactose or mannitol. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the human adult, each dose per person is generally between 0.005 and 5 mg by oral administration in the treatment of hypertension, between 0.005 and 5 mg by oral administration in the treatment of disorders of the peripheral circulation, and between 0.01 and 50 mg by oral administration in the prevention of cerebral thrombosis, myocardial infarction and arteriosclerosis The following Example illustrates pharmaceutical compositions according to the invention.

EXAMPLE 11

(13E)-(6RS,9α,11α,15S)-6,9-Epoxy-11,15-dihydroxy-15-(3-propylcyclopentyl)-16,17,18,19,20-pentanorprost-13-enoic acid methyl ester (10 mg) was dissolved in ethanol (10 ml), mixed with mannitol (18.5 g), sieved through a 30-mesh sieve, dried at 30° C. for 90 minutes and again sieved through a 30-mesh sieve. Aerosil (microfine silica, 200 mg) was added and the powder obtained was machine filled into one hundred No. 2 hard gelatin capsules to give capsules each containing 100 μg of (13E)-(6RS,9α, 11α,15S)-6,9-epoxy-11,15-dihydroxy-15-(3-propylcyclopentyl)-16,17,18,19,20-pentanorprost-13-enoic acid methyl ester, which after swallowing of the capsule is released into the stomach. "Aerosil" is a registered Trade Mark.

We claim:

1. A prostaglandin analog of the formula:

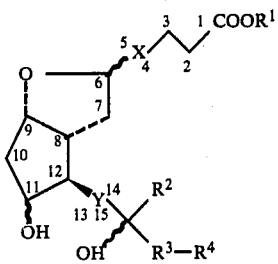

wherein X represents the trans-vinylene group, y represents the trans-vinylene group or the ethylene group, $R^1$ represents a hydrogen atom or a straight- or branched-chain alkyl group containing from 1 to 12 carbon atoms, $R^2$ represents a hydrogen atom or a methyl or ethyl group, $R^3$ represents a single bond or a straight- or branched-chain alkylene group containing from 1 to 4 carbon atoms, $R^4$ represents a hydrogen atom, a straight- or branched-chain alkyl group containing from 1 to 8 carbon atoms, a cycloalkyl group containing from 4 to 7 carbon atoms unsubstituted or substituted by at least one straight- or branched-chain alkyl group containing from 1 to 8 carbon atoms, or a phenyl or phenoxy group unsubstituted or carrying at least one substituent selected from halogen atoms, the trifluoromethyl group and alkyl groups containing from 1 to 3 carbon atoms, and the wavy line attached to the carbon atoms in positions 6, 11 and 15 depicted in the formula represents α- or β-configuration or mixtures thereof, cyclodextrin clathrates thereof and, when $R^1$ represents a hydrogen atom, non-toxic salts thereof.

2. A prostaglandin analog according to claim 1 wherein $R^4$ represents a hydrogen atom, a straight- or branched-chain alkyl group containing from 1 to 8 carbon atoms, or a phenyl or phenoxy group unsubstituted or carrying at least one substituent selected from halogen atoms, the trifluoromethyl group and alkyl groups containing from 1 to 3 carbon atoms and cyclodextrin clathrates thereof and, when $R^1$ represents a hydrogen atom, non-toxic salts thereof."

3. A prostaglandin analog according to claim 1 wherein Y represents the trans-vinylene group and, when $R^1$ represents a hydrogen atom, non-toxic salts thereof.

4. A prostaglandin analog according to claim 1, wherein $R^1$ represents the methyl group.

5. A prostaglandin analog according to claim 1, wherein $-R^3-R^4$ represents pentyl, 1-methylpentyl, 2-methylpentyl, 3-methylpentyl, 4-methylpentyl, 1,1-dimethylpentyl, 1,2-dimethylpentyl, 1,4-dimethylpentyl, 1-ethylpentyl, 2-ethylpentyl, 1-propylpentyl, 2-propylpentyl, hexyl, 1-methylhexyl, 2-methylhexyl, 1,1-dimethylhexyl, 1-ethylhexyl, 2-ethylhexyl, heptyl, 2-ethylheptyl, nonyl, undecyl, cyclobutyl, (1-propyl)cyclobutyl, (1-butyl)cyclobutyl, (1-pentyl)cyclobutyl, (2-propyl)cyclobutyl, (3-ethyl)-cyclobutyl, (3-propyl)cyclobutyl, cyclopentyl, 1-cyclopentylethyl, 2-cyclopentylethyl, 2-cyclopentylpropyl, (3-ethyl)cyclopentyl, (3-propyl)cyclopentyl, (3-butyl)-cyclopentyl, (1-methyl-3-propyl)cyclopentyl, (2-methyl-3-propyl)cyclopentyl, cyclohexyl, (3-ethyl)cyclohexyl, (4-methyl)cyclohexyl, (4-ethyl)cyclohexyl, (4-propyl)-cyclohexyl, (2,6-dimethyl)cyclohexyl, cyclohexylmethyl, (1-methylcyclohexyl)methyl, 1-cyclohexylethyl, 2-cyclohexylethyl, (1-methyl-1-cyclohexyl)ethyl, 1-cycloheptylethyl, phenyl, benzyl, 1-phenylethyl, 2-phenylethyl, 1-phenylpentyl, phenoxymethyl, (3-chlorophenoxy)methyl, (4-chlorophenoxy)-methyl or (3-trifluoromethylphenoxy)methyl.

6. A prostaglandin analog according to claim 1, which is (4E,13E)-(6RS,9α,11α,15S)-6,9-epoxy-11,15-dihydroxyprosta-4,13-dienoic acid methyl ester and cyclodextrin clathrates thereof.

7. A prostaglandin analog according to claim 1, which is (4E,13E)-(6RS,9α,11α,15S)-6,9-epoxy-11,15-dihydroxyprosta-4,13-dienoic acid and cyclodextrin clathrates and non-toxic salts thereof.

8. A pharmaceutical composition for the treatment of hypertension which comprises, as active ingredient, an effective amount of at least one prostaglandin analog as claimed in claim 1, or a cyclodextrin clathrate of such a prostaglandin analog, or when $R^1$ in the general formula depicted in claim 1 represents a hydrogen atom—a non-toxic salt of such a prostaglandin acid, in association with a pharmaceutical carrier or coating.

9. A pharmaceutical composition for the treatment of disorders of the peripheral circulation which comprises, as active ingredient, an effective amount of at least one prostaglandin analog as claimed in claim 1, or a cyclodextrin clathrate of such a prostaglandin analog, or when $R^1$ in the general formula depicted in claim 1 represents a hydrogen atom —a non-toxic salt of such a prostaglandin acid, in association with a pharmaceutical carrier or coating.

10. A pharmaceutical composition for the prevention and treatment of cerebral thrombosis which comprises, as active ingredient, an effective amount of at least one prostaglandin analog as claimed in claim 1, or a cyclodextrin clathrate of such a prostaglandin analog, or when $R^1$ in the general formula depicted in claim 1 represents a hydrogen atom —a non-toxic salt of such a prostaglandin acid, in association with a pharmaceutical carrier or coating.

11. A pharmaceutical composition for the prevention and treatment of myocardial infarction which comprises, as active ingredient, an effective amount of at least one prostaglandin analog as claimed in claim 1, or a cyclodextrin clathrate of such a prostaglandin analog, or when $R^1$ in the general formula depicted in claim 1 represents a hydrogen atom —a non-toxic salt of such a prostaglandin acid, in association with a pharmaceutical carrier or coating.

12. A pharmaceutical composition for the prevention and treatment of arteriosclerosis which comprises, as active ingredient, an effective amount of at least one prostaglandin analog as claimed in claim 1, or a cyclodextrin clathrate of such a prostaglandin analog, or when $R^1$ in the general formula depicted in claim 1 represents a hydrogen atom—a non-toxic salt of such a prostaglandin acid, in association with a pharmaceutical carrier or coating.

13. A compound of the formula:

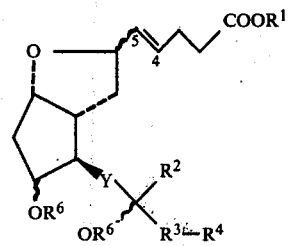

IIIC wherein $R^6$ represents a tetrahydropyran-2-yl group unsubstituted or substituted by at least one alkyl group, or a tetrahydrofuran-2-yl or 1-ethoxyethyl group, the other symbols are as defined in claim 1, and the depicted $C_4$–$C_5$ double bond is trans.

* * * * *